US011807886B2

(12) United States Patent
Law et al.

(10) Patent No.: US 11,807,886 B2
(45) Date of Patent: Nov. 7, 2023

(54) PROCESS FOR THE PREPARATION OF COPOLYMERS DERIVED FROM 2,4- OR 2,5-PYRIDINEDICARBOXYLIC ACID

(71) Applicant: Biome Bioplastics Limited, Southampton (GB)

(72) Inventors: Paul Law, Southampton (GB); Paul Mines, Southampton (GB); Timothy Bugg, Coventry (GB)

(73) Assignee: BIOME BIOPLASTICS LIMITED, Southampton (GB)

( * ) Notice: Subject to any disclaimer, the term of this patent is extended or adjusted under 35 U.S.C. 154(b) by 579 days.

(21) Appl. No.: 16/814,794

(22) Filed: Mar. 10, 2020

(65) Prior Publication Data

US 2020/0208183 A1   Jul. 2, 2020

Related U.S. Application Data

(62) Division of application No. 15/580,254, filed as application No. PCT/EP2016/063779 on Jun. 15, 2016, now Pat. No. 10,612,057.

(30) Foreign Application Priority Data

Jun. 15, 2015 (GB) .................................. 1510461

(51) Int. Cl.
| | |
|---|---|
| C12P 17/12 | (2006.01) |
| C12P 7/44 | (2006.01) |
| C08G 63/685 | (2006.01) |
| C12P 7/50 | (2006.01) |
| C07D 213/803 | (2006.01) |
| C08G 63/78 | (2006.01) |
| C12N 9/02 | (2006.01) |
| C12P 7/42 | (2006.01) |

(52) U.S. Cl.
CPC .......... *C12P 17/12* (2013.01); *C07D 213/803* (2013.01); *C08G 63/6856* (2013.01); *C08G 63/78* (2013.01); *C12N 9/0069* (2013.01); *C12P 7/42* (2013.01); *C12P 7/44* (2013.01); *C12P 7/50* (2013.01); *C12Y 113/11* (2013.01)

(58) Field of Classification Search
None
See application file for complete search history.

(56) References Cited

U.S. PATENT DOCUMENTS

| 3,035,025 A | 5/1962 | Broadhead et al. |
| 10,612,057 B2 * | 4/2020 | Law ........................ C12P 17/12 |

FOREIGN PATENT DOCUMENTS

| EP | 0390102 | 10/1990 |
| GB | 790940 | 2/1958 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Barry et al., "Characterizing the Promiscuity of LigAB, a Lignin Catabolite Degrading Extradiol Dioxygenase from Sphingomonas paucimobilis SYK-6", Biochemistry, 2013, 52(38): 6724-6736.
Eaton et al., "Metabolism of Dibutylphthalate and Phthalate by Micrococcus sp Strain 12B", Journal of Bacteriology, 1982, 151(1): 48-57.
Evans, "The Microbiological Degradation of Aromatic Compounds", J. gen. Microbiol., 1963, 32: 177-184.
Kasai et al., "Uncovering the Protocatechuate 2,3-Cleavage Pathway Genes", Journal of Bacteriology, 2009, 191(21): 6758-6768.
Masai et al., "Genetic and Biochemical Characterization of 4-Carboxy-2-Hydroxymuconate-6-Semialdehyde Dehydrogenase and Its Role in the Protocatechuate 4,5-Cleavage Pathway in Sphingomonas paucimobilis SYK-6", Journal of Bacteriology, 2000, 182(23): 6651-6658.
Database WPI Week 199445, Thomson Scientific, XP002761492 & JP H06 287287 (Toray Ind Inc), 1994.
Sainsbury et al., "Breaking Down Lignin to High-Value Chemicals: The Conversion of Lignocellulose to Vanillin in a Gene Deletion Mutant of Rhodococcus jostii RHA1", ACS Chemical Biology, 2013, 8: 2151-2156.
Lv et al., "Interaction among multiple microorganisms and effects of nitrogen and carbon supplementations on lignin degradation", Bioresource Technology, 2013, 155: 144-151.
Yamanashi et al., "In vitro reconstitution of the catabolic reactions catalyzed by PcaHG, PcaB, and PcaL: the protocatechuate branck of the β-ketoadipate pathway in Rhodococcus jostii RHA1" 79(5) Bioscience, Biotechnology, and Biochemistry, 2015, 79(5): 830-835.
An et al., "Structures and Luminescent Properties of Two 2D Coordination Polymers Containing Tb(lll) or Dy(III) Ions", J. Fluoresc, 2014, 24:425-429.

* cited by examiner

*Primary Examiner* — Christian L Fronda
(74) *Attorney, Agent, or Firm* — James S. Keddie; Bozicevic, Field & Francis LLP

(57) ABSTRACT

The present invention relates to processes for the formation of pyridinedicarboxylic acid (PDCA), in particular, 2,4-pyridinedicarboxylic acid (2,4-PDCA) and 2,5-pyridinedicarboxylic acid (2,5-PDCA), and mono- and diester derivatives thereof, from 3,4-dihydroxybenzoic acid, via a biocatalytic reaction using, for example, a protocatechuate dioxygenase such as protocatechuate 4,5-dioxygenase or protocatechuate 2,3-dioxygenase, and a nitrogen source. The invention also relates to copolymers that comprise the pyridinedicarboxylic acid monomers and derivatives thereof, processes for the formation of the copolymers and uses for the copolymers.

15 Claims, 16 Drawing Sheets

PROCESS FOR THE PREPARATION OF COPOLYMERS DERIVED FROM 2,4- OR 2,5-PYRIDINEDICARBOXYLIC ACID

CROSS-REFERENCE TO RELATED APPLICATIONS

This application is a divisional of U.S. application Ser. No. 15/580,254, filed on Dec. 6, 2017, which is a § 371 national phase of International Application No. PCT/EP2016/063779, filed on Jun. 15, 2016, which claims the benefit of United Kingdom Patent Application No. 1510461.5, filed on Jun. 15, 2015, which applications are incorporated by reference herein.

The present invention relates to new processes for the formation of pyridinedicarboxylic acid (PDCA), in particular, 2,4-pyridinedicarboxylic acid (2,4-PDCA) and 2,5-pyridinedicarboxylic acid (2,5-PDCA), and mono- and diester derivatives thereof, copolymers that comprise pyridinedicarboxylic acid monomers and derivatives thereof, processes for the formation of the copolymers and uses for the copolymers.

Due to their versatility, polymers, such as plastics, have found wide ranging application in modern society, and can be found in products ranging from carbonated drinks bottles to mobile phones and surgical equipment. PET (polyethylene terephthalate) is one of the most dominant plastics on the market. The annual worldwide production of PET is approximately 53.3 million tonnes, which makes up 18% of global polymer production. However, as PET is highly stable, it is resistant to biodegradation which poses a significant environmental threat. PBAT (polybutylene adipate co-terephthalate) is known to be flexible, tough and most importantly biodegradable. PBAT can be blended with other biodegradable polymers and can potentially be used as substitutes for industry standard plastics, such as PET.

Terephthalic acid (TPA) is a precursor used in the production of PET and PBAT. TPA is manufactured by oxidation of para-xylene, which is derived from petrochemicals. As oil reserves represent a finite source of petrochemicals, there is considerable interest in the development of bio-based plastics derived from biomass, particularly plastics that are biodegradable.

In a first aspect of the invention, pyridinedicarboxylic acid (PDCA) is formed from 3,4-dihydroxybenzoic acid (protocatechuic acid; PCA). The 3,4-dihydroxybenzoic acid may be formed from a plant source, preferably from a source of lignin. In a particular feature, PDCA is formed from lignin.

*Rhodococcus jostii* RHA1 is a bacterial lignin degrader in which extracellular peroxidase enzyme DypB has been shown to oxidise lignin. Deletion of the vdh gene encoding vanillin dehydrogenase in *R. jostii* gives a gene deletion mutant that, upon growth in minimal media containing, for instance, wheat straw lignocellulose, generates up to 96 mg/L vanillin after 6 days fermentation (see Sainsbury et al. *ACS Chem. Biol.* 2013, 8, 2151-2156).

The conversion of vanillin to 3,4-dihydroxybenzoic acid appears to be a central pathway involved in lignin metabolism. 3,4-Dihydroxybenzoic acid is normally metabolised via ortho-cleavage to the β-keto-adipate pathway. However, it has been found that a gene introduction approach can be used to reroute the aromatic degradation pathways downstream from lignin oxidation. In particular, protocatechuate dioxygenases can be used to form ring-opened 3,4-dihydroxybenzoic acid products, such as extradiol ring cleavage products, which can be cyclised with a nitrogen source to form pyridinedicarboxylic acids.

If the source of nitrogen is present during the ring-opening process, i.e. in the fermentation broth, then the desired pyridinedicarboxylic acid will be formed in situ. Thus, the need to isolate the intermediate ring-opened product prior to the cyclisation step is avoided. There is therefore provided a novel, convenient and efficient one-pot two-step process for the formation of pyridinedicarboxylic acids from 3,4-dihydroxybenzoic acid (protocatechuic acid), which are useful in the formation of the copolymers of the invention (as defined below).

In a feature of the first aspect of the invention, pyridinedicarboxylic acid is provided using suitable bacteria, for instance *R. jostii*, into which genes for the protocatechuate dioxygenases have been introduced, either into the genome or by way of a separate expression vector. Introduction of the genes can be by any suitable method, such as by electroporation. It is also contemplated that the conversion of 3,4-dihydroxybenzoic acid (protocatechuic acid) into pyridinedicarboxylic acid (PDCA) can comprise an enzymatic process that uses the dioxygenases.

In a particular feature of the first aspect of the invention, the process is for the formation of 2,4-pyridinedicarboxylic acid (2,4-PDCA) or 2,5-pyridinedicarboxylic acid (2,5-PDCA) from 3,4-dihydroxybenzoic acid comprising the steps of
(i) using a protocatechuate dioxygenase to form a ring-opened product of 3,4-dihydroxybenzoic acid; and
(ii) cyclising the ring-opened product of step (i) with a nitrogen source to form the pyridinedicarboxylic acid.

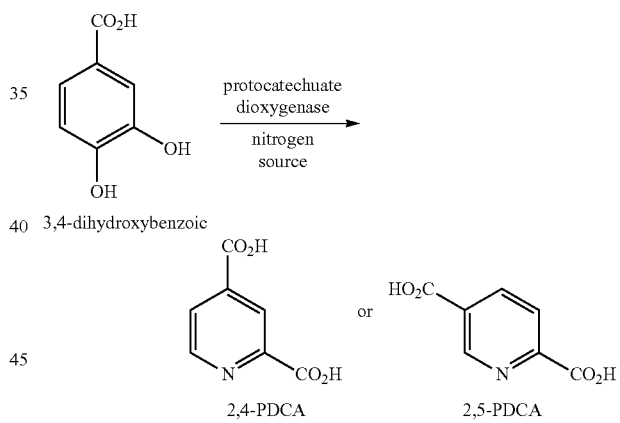

It is preferable that the nitrogen source of step (ii) is present during step (i).

When the pyridinedicarboxylic acid to be formed is 2,4-pyridinedicarboxylic acid, the protocatechuate dioxygenase may be protocatechuate 4,5-dioxygenase, and the ring-opened product may be 4-carboxy-2-hydroxymuconate-6-semialdehyde (CHMS).

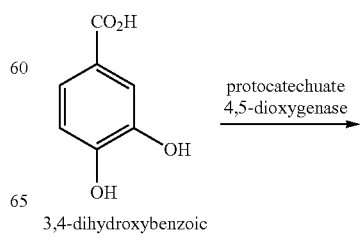

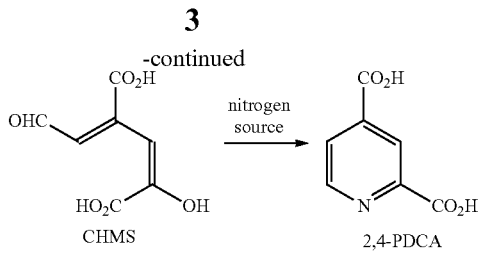

When the pyridinedicarboxylic acid (PDCA) to be formed is 2,5-pyridinedicarboxylic acid, the protocatechuate dioxygenase may be protocatechuate 2,3-dioxygenase, and the ring-opened product may be 5-carboxy-2-hydroxymuconate-6-semialdehyde (5-CHMS).

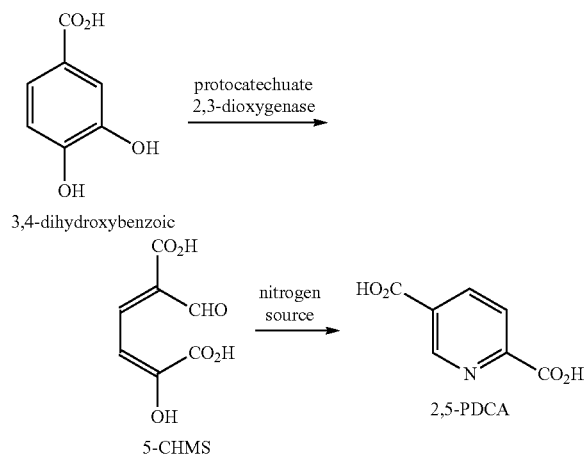

Suitable nitrogen sources include ammonium salts, such as ammonium chloride and ammonium hydroxide, or ammonia. It is preferred that the nitrogen source is ammonium chloride, which is used in bacterial fermentations. The nitrogen source may be provided in a solution, preferably an aqueous solution. Preferably, the nitrogen source may be provided in the solution in an amount of from about 1 mg/L to about 200 g/L, such as from about 200 mg/L to about 100 g/L, for example from about 500 mg/L to about 10 g/L, preferably from about 800 mg/L to about 5 g/L.

The protocatechuate dioxygenase can be provided in a purified, or partially purified form or as a component of a cell lysate. Alternatively, as previously discussed, the production of pyridinedicarboxylic acid can be catalysed using suitable bacteria, for instance R. jostii, into which genes for the protocatechuate dioxygenases have been introduced, either into the genome or by way of a separate expression vector. Thus, the pyridinedicarboxylic acid may be provided by the addition of at least one bacterium, preferably Rhodococcus jostii modified to express protocatechuate dioxygenase, to the 3,4-pyridinedicarboxylic acid.

The 3,4-dihydroxybenzoic acid may be provided in a solution in step (i), preferably an aqueous solution. Preferably, 3,4-dihydroxybenzoic acid may be provided in a solution at a concentration of from about 1 mM to about 1,000 mM, such as from about 10 mM to about 750 mM, for instance from about 50 mM to about 500 mM.

A buffer may be provided in the process of the first aspect of the invention in step (i) and/or step (ii). The buffer may maintain a pH of from about 6 to about 8 in the process. Any suitable buffer can be used in the reaction. Particularly useful buffers are phosphate buffers, such as a potassium phosphate buffer. The pH may be determined by any known means. It is preferred that the pH is determined using a pH meter and a probe.

Thus, each of the processes of the present invention is preferably carried out in a buffered reaction mixture with a pH of 6 to 8. Preferably the reaction mixture is buffered with a phosphate buffer, more preferably potassium phosphate buffer. The pH may be determined by any known means. It is preferred that the pH is determined using a pH meter and a probe.

The processes of the first aspect of the invention can be conducted at any suitable temperature. Suitable temperatures for the process may be from 0° C. to about 60° C., such as from about 20° C. to about 50° C., for instance from about 30° C. to about 40° C. It is particularly preferred that steps (ii) and/or (iii) are carried out at about 37° C. The temperature may be maintained by any suitable means, for instance using a shaking incubator.

Any suitable method of isolating the pyridinedicarboxylic acids can be used. It is preferred that the reaction media is centrifuged and the supernatant applied to an ion exchange column, i.e. an anion exchange column, such as an Amberlite™ IRA900 anion exchange column. Pyridinedicarboxylic acids may also be isolated by chromatography, such as reverse-phase chromatography using a C18 column and a gradient of water/0.1% trifluoroacetic acid (solvent A) and methanol/0.1% trifluoroacetic acid (solvent B).

Lignin, lignocellulose, vanillic acid and/or vanillin can be converted into 2,4-pyridinedicarboxylic acid and 2,5-pyridinedicarboxylic acid as set out in Scheme A below.

Scheme A - Biotransformation of lignin into 2,4-PDCA or 2,5-PDCA using modified R. jostii.

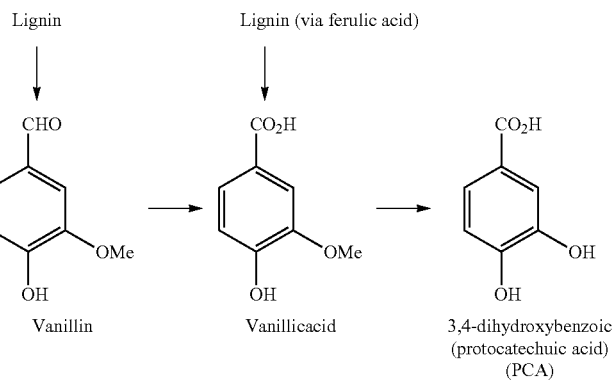

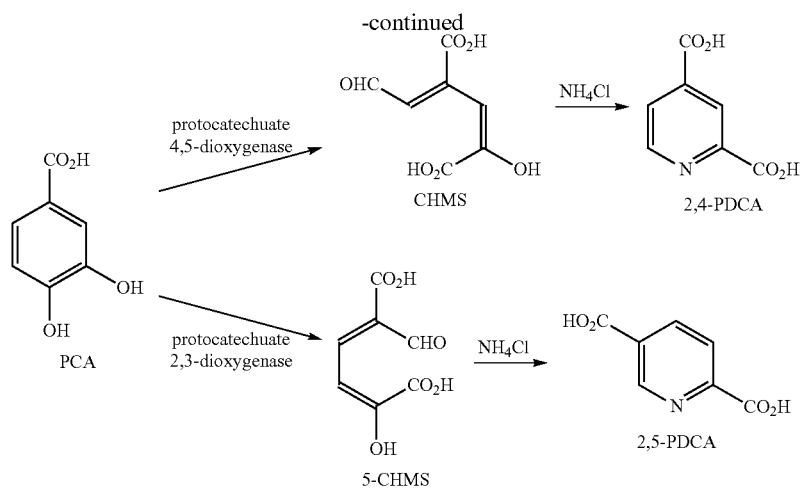

*R. jostii* can utilise a variety of carbon sources in the formation of pyridinedicarboxylic acids, such as 3,4-dihydroxybenzoic acid (protocatechuic acid), vanillic acid, sources of lignin (e.g. Kraft lignin or from bioethanol production), or wheat straw lignocellulose, e.g. milled wheat straw lignocellulose. Typically, M9 minimal media containing 3,4-dihydroxybenzoic acid, vanillic acid, lignin (i.e. Kraft lignin) or wheat straw lignocellulose, and a suitable nitrogen source can be used. It is preferred that the carbon source is lignin.

Thus, the 2,4-PDCA or 2,5-PDCA can be obtained by contacting protocatechuic acid with protocatechuate dioxygenase or *Rhodococcus jostii* modified to express protocatechuate dioxygenase in the presence of a nitrogen source.

Alternatively, the 2,4-PDCA or 2,5-PDCA can be obtained by contacting vanillic acid with protocatechuate dioxygenase or *Rhodococcus jostii* modified to express protocatechuate dioxygenase in the presence of a nitrogen source.

In view of the above, in a feature of the first aspect of the invention, the 3,4-dihydroxybenzoic acid is formed from vanillic acid. The vanillic acid can be formed from vanillin, which in turn is known to be formed from lignin. Such process may be carried out by bacterial or enzymatic processes, which are well known to those skilled in the art.

When vanillic acid is used as a carbon source, it can be present in an amount of from about 0.01% to about 5%, preferably from about 0.05% to about 0.25%, more preferably at about 0.1% w/v in aqueous media. When wheat straw lignocellulose is used as a carbon source, it can be milled wheat straw lignocellulose and can be present in an amount of from about 0.1% to about 5%, preferably from about 0.5% to about 2.5%, more preferably about 1% w/v in aqueous media. When Kraft lignin is used as the carbon source, it can be present in an amount of from about 0.01% to about 5%, preferably from about 0.1% to about 2%, more preferably at about 0.5% w/v in aqueous media.

Fermentation of culture media containing *R. jostii* can be carried out under suitable conditions, and for a suitable time, which will be known to the skilled person. Suitable times are from about 1 hour to about 20 days, preferably from about 3 hours to 10 days, and most preferably from about 5 hours to 7 days.

The present invention provides a novel biocatalytic route to pyridinedicarboxylic acids from renewable feedstocks, such as lignin, highlighting the opportunity for bioconversion of lignin into aromatic products using biotechnology. Since lignin is generated as a by-product of cellulosic bioethanol production and paper/pulp manufacture, it may be possible to combine this technology with an existing industrial process in order to generate value-added products from the lignin stream.

In a second aspect of the invention there is provided a process for the formation of a mono- or diester of 2,4-pyridinedicarboxylic acid (2,4-PDCA) and/or 2,5-pyridinedicarboxylic acid (2,5-PDCA) from 2,4-pyridinedicarboxylic acid and/or 2,5-pyridinedicarboxylic acid, comprising the step of (i) providing 2,4-pyridinedicarboxylic acid and/or 2,5-pyridinedicarboxylic acid; and
(ii) adding an alcohol and a catalyst to the pyridinedicarboxylic acid provided in step (i), wherein the 2,4-pyridinedicarboxylic acid and/or 2,5-pyridinedicarboxylic acid is obtained by a process as defined in the first aspect of the invention.

Any suitable alcohol can be used. Suitable alcohols include straight, or where possible branched or cyclic, $C_1$ to $C_6$ alkyl group, such as a $C_1$ to $C_4$ alkyl group, preferably a $C_1$ or $C_2$ alkyl group, substituted by an —OH group. Methanol and ethanol are preferred. Ethanol is particularly preferred. Therefore, the second aspect of the invention relates to a process for the formation of a mono- or diester of 2,4-pyridinedicarboxylic acid (2,4-PDCA) or 2,5-pyridinedicarboxylic acid (2,5-PDCA) selected from the group consisting of

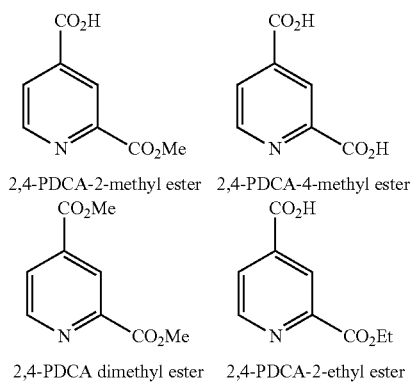

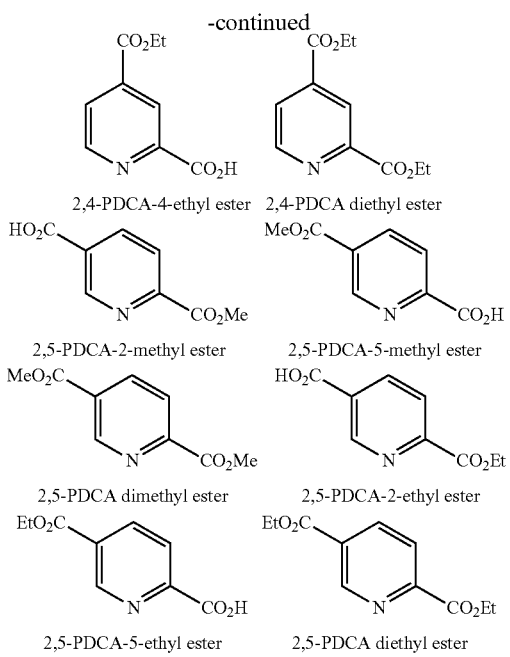

2,4-PDCA-4-ethyl ester   2,4-PDCA diethyl ester
2,5-PDCA-2-methyl ester  2,5-PDCA-5-methyl ester
2,5-PDCA dimethyl ester  2,5-PDCA-2-ethyl ester
2,5-PDCA-5-ethyl ester   2,5-PDCA diethyl ester or a combination thereof
comprising the step of
(i) providing 2,4-pyridinedicarboxylic acid and/or 2,5-pyridinedicarboxylic acid; and
(ii) adding methanol or ethanol,
wherein the 2,4-pyridinedicarboxylic acid and/or 2,5-pyridinedicarboxylic acid is obtained by a process as defined in the first aspect of the invention.

Any suitable catalyst may be used. Preferred catalysts are organic acids or inorganic acids, such as mineral acids. Typical organic acids include acetic acid, trifluoroacetic acid or formic acid; typical inorganic acids include hydrochloric acid and sulfuric acid. Inorganic acids are preferred, with sulfuric acid being particular preferred.

In a third aspect of the invention, there is provided a process for the formation of a copolymer comprising the polymerisation product of
(a) at least one 2,4-pyridinedicarboxylic acid (2,4-PDCA) and/or 2,5-pyridinedicarboxylic acid (2,5-PDCA) or a mono- or diester of 2,4-pyridinedicarboxylic acid and/or 2,5-pyridinedicarboxylic acid;
(b) at least one diol; and
(c) optionally, at least one aliphatic dicarboxylic acid or a mono- or diester derivative thereof
wherein the process comprises reacting together components (a), (b) and optionally (c), and wherein the 2,4-pyridinedicarboxylic acid and/or 2,5-pyridinedicarboxylic acid is obtained by a process as defined in the first aspect of the invention, and/or the mono- or diester of 2,4-pyridinedicarboxylic acid and/or 2,5-pyridinedicarboxylic acid is obtained by a process as defined in the second aspect of the invention.

This process is referred to herein as a process of the invention. A copolymer formed by said process is referred to as a copolymer of the invention.

The process may form a copolymer comprising the polymerisation product of
(a) at least one 2,4-pyridinedicarboxylic acid and/or 2,5-pyridinedicarboxylic acid or a mono- or diester of 2,4-pyridinedicarboxylic acid and/or 2,5-pyridinedicarboxylic acid;
(b) at least one diol; and
(c) at least one aliphatic dicarboxylic acid or a mono- or diester derivative thereof
wherein the 2,4-pyridinedicarboxylic acid and/or 2,5-pyridinedicarboxylic acid is obtained by a process as defined in the first aspect of the invention, and/or the mono- or diester of 2,4-pyridinedicarboxylic acid and/or 2,5-pyridinedicarboxylic acid is obtained by a process as defined in the second aspect of the invention.

The process may form a copolymer consisting essentially of the polymerisation product of
(a) at least one 2,4-pyridinedicarboxylic acid and/or 2,5-pyridinedicarboxylic acid or a mono- or diester of 2,4-pyridinedicarboxylic acid and/or 2,5-pyridinedicarboxylic acid;
(b) at least one diol; and
(c) at least one aliphatic dicarboxylic acid or a mono- or diester derivative thereof
wherein the 2,4-pyridinedicarboxylic acid and/or 2,5-pyridinedicarboxylic acid is obtained by a process as defined in the first aspect of the invention, and/or the mono- or diester of 2,4-pyridinedicarboxylic acid and/or 2,5-pyridinedicarboxylic acid is obtained by a process as defined in the second aspect of the invention.

Such copolymers may exhibit properties that are similar to PBAT, such as being flexible, tough and biodegradable, and can be used either as a replacement for PBAT or in combination with PBAT.

As set out above, the process may form a copolymer that comprises the polymerisation product of
(a) at least one 2,4-pyridinedicarboxylic acid and/or 2,5-pyridinedicarboxylic acidor a mono- or diester of 2,4-pyridinedicarboxylic acid and/or 2,5-pyridinedicarboxylic acid; and
(b) at least one diol
wherein the 2,4-pyridinedicarboxylic acid and/or 2,5-pyridinedicarboxylic acid is obtained by a process as defined in the first aspect of the invention, and/or the mono- or diester of 2,4-pyridinedicarboxylic acid and/or 2,5-pyridinedicarboxylic acid is obtained by a process as defined in the second aspect of the invention.

In particular, the process may form a copolymer consisting essentially of the polymerisation product of
(a) at least one 2,4-pyridinedicarboxylic acid and/or 2,5-pyridinedicarboxylic acid or a mono- or diester of 2,4-pyridinedicarboxylic acid and/or 2,5-pyridinedicarboxylic acid; and
(b) at least one diol
wherein the 2,4-pyridinedicarboxylic acid and/or 2,5-pyridinedicarboxylic acid is obtained by a process as defined in the first aspect of the invention, and/or the mono- or diester of 2,4-pyridinedicarboxylic acid and/or 2,5-pyridinedicarboxylic acid is obtained by a process as defined in the second aspect of the invention.

Such processes may form copolymers that may exhibit properties that are similar to PET, such as being semi-rigid to rigid, and can be used either as a replacement for PET or in combination with PET.

The 2,4-pyridinedicarboxylic acid and/or 2,5-pyridinedicarboxylic acid or a mono- or diester of 2,4-pyridinedicarboxylic acid and/or 2,5-pyridinedicarboxylic acid, diol and aliphatic dicarboxylic acid or a mono- or diester derivative thereof can be referred to as monomers. The term "monomer" is one of the art. For the avoidance of any doubt, monomers are molecules that can be bonded to other molecules to form a polymer.

The term "copolymer" is one of the art. It refers to a polymer comprising two or more different monomer units that are polymerised in a process called copolymerisation. Since a copolymer comprises at least two different monomer units, copolymers can be classified based on how the monomer units are arranged to form a polymer chain. Those classifications include "alternating copolymers" (in which the monomers units repeat with an regular alternating pattern), "periodic copolymers" (in which the monomers units are arranged with a repeating sequence), "statistical copolymers" (in which the sequence of monomer units follows a statistical rule), "random copolymers" (in which the monomer units are attached in a random order), and "block copolymers" (in which two or more homopolymer subunits are linked).

The copolymers of the invention may be a block copolymer, alternating copolymer, periodic copolymer, statistical copolymer or random copolymer. It is preferred that the copolymers are random copolymers.

The term "consists essentially of" in this context means that copolymer of the invention is substantially free from any other monomer. That is, the copolymer of the invention comprises greater than about 90%, such as greater than about 95%, preferably greater than about 98%, and most preferably greater than about 99% of the listed monomers.

The term "at least one" is synonymous with "one or more", i.e. one, two, three, four, five, six, or more.

The term "pyridinedicarboxylic acid (PDCA) or a mono- or diester of pyridinedicarboxylic acid" is a compound of formula

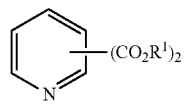

wherein each $R^1$ independently represents H or a straight, or where possible branched or cyclic, $C_1$ to $C_6$ alkyl group, such as a $C_1$ to $C_4$ alkyl group, preferably a H or a $C_1$ or $C_2$ alkyl group. It is preferable that the two $R^1$ groups are the same. It will be understood that the two ($CO_2R^1$) groups can be located at any position on the pyridine ring.

In a feature of the third aspect of the invention, the 2,4-pyridinedicarboxylic acid and/or 2,5-pyridinedicarboxylic acid or a mono- or diester of 2,4-pyridinedicarboxylic acid and/or 2,5-pyridinedicarboxylic acid is

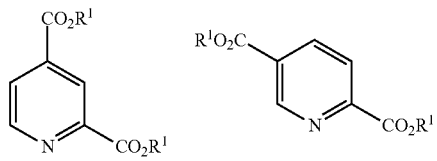

wherein each $R^1$ independently represents H or a straight, or where possible branched or cyclic, $C_1$ to $C_6$ alkyl group, such as a $C_1$ to $C_4$ alkyl group, preferably a H or a $C_1$ or $C_2$ alkyl group. It is preferable that the two $R^1$ groups are the same.

2,4-Pyridinedicarboxylic acid and/or 2,5-pyridinedicarboxylic acid and mono- or diesters of 2,4-pyridinedicarboxylic acid and/or 2,5-pyridinedicarboxylic acid that are of particular interest are 2,4-pyridinedicarboxylic acid (2,4-PDCA), 2,4-PDCA-2-methyl ester, 2,4-PDCA-4-methyl ester, 2,4-PDCA dimethyl ester, 2,4-PDCA-2-ethyl ester, 2,4-PDCA-4-ethyl ester, 2,4-PDCA diethyl ester, 2,5-pyridinedicarboxylic acid (2,5-PDCA), 2,5-PDCA-2-methyl ester, 2,5-PDCA-5-methyl ester, 2,5-PDCA dimethyl ester, 2,5-PDCA-2-ethyl ester, 2,5-PDCA-5-ethyl ester, 2,5-PDCA diethyl ester and combinations thereof, with 2,4-PDCA diethyl ester and 2,5-PDCA diethyl ester being particularly preferred. 2,4-Pyridinedicarboxylic acid and 2,5-pyridinedicarboxylic acid are provided according to the first aspect of the invention. The mono- and diesters of 2,4-pyridinedicarboxylic acid and 2,5-pyridinedicarboxylic acid are provided according to the second aspect of the invention.

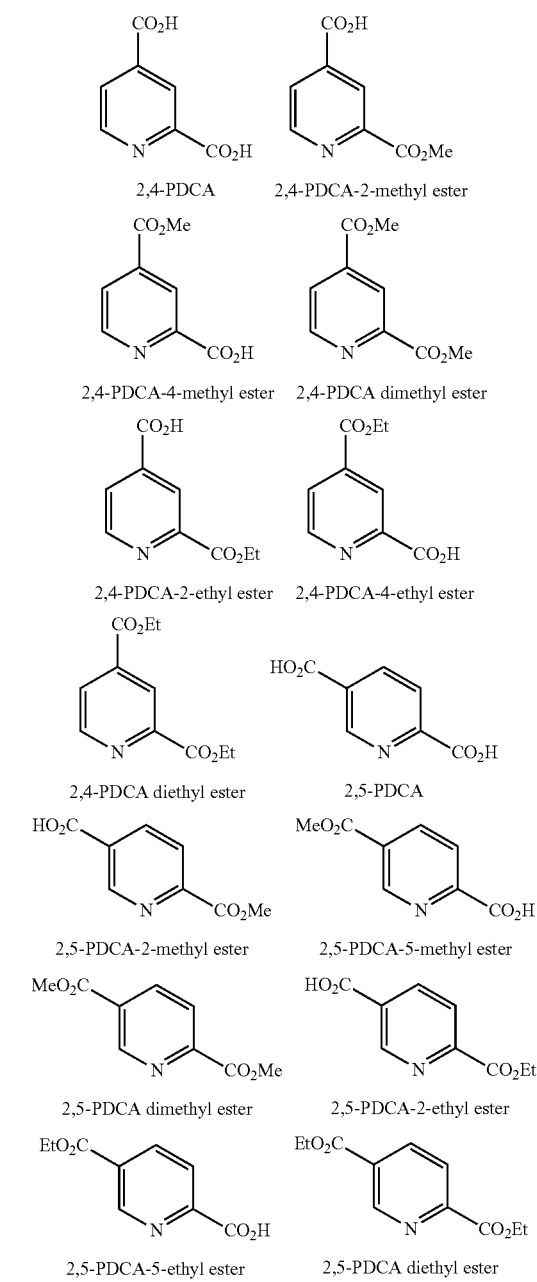

The term "diol" refers to a compound of formula

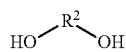

wherein $R^2$ is a straight or, where possible, branched or cyclic $C_2$ to $C_{10}$ saturated alkylene, preferably a $C_2$ to $C_6$ saturated alkylene, and more preferably $C_2$ to $C_4$ saturated alkylene, or a mixture thereof.

The term "alkylene" refers to an alkyl diradical, including straight-chain, and, where possible, branched-chain and cyclic groups. Where the alkylene group refers to a range, such as $C_2$ to $C_{12}$, it is to be understood that it includes each member of the range, i.e. $C_2$, $C_3$, $C_4$, $C_5$, $C_6$, $C_7$, $C_8$, $C_9$, $C_{10}$, $C_{11}$, and/or $C_{12}$.

The skilled person will understand that for a diol to be branched or cyclic then at least three carbon unit are required. Non-limiting examples of branched diols useful in the invention are 1,2-propanediol, 1,2-butanediol, 2,2-dimethyl-1,3-propanediol. Non-limiting examples of cyclic diols useful in the invention are 1,2-cyclopentanediol, 1,2-cyclobutanediol, and 1,2-cyclopentanediol. The diols may also be branched, cyclic diols, e.g. 3-methyl-1,2-cyclopropanediol.

In a particular feature, the alkylene group present in the diol is unbranched.

In a preferred feature of the third aspect of the invention, the diol is 1,2-ethanediol, 1,4-butanediol, or combinations thereof. Copolymers formed from 1,4-butanediol or 1,2-ethanediol may exhibit properties that are similar to PBAT or PET, respectively, as discussed above.

The term "aliphatic dicarboxylic acid or a mono- or diester derivative thereof" refers to a compound of formula

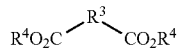

wherein $R^3$ is a straight or, where possible, branched or cyclic, $C_1$ saturated or $C_2$ to $C_{10}$ saturated or unsaturated alkylene, preferably $C_2$ to $C_6$ saturated or unsaturated alkylene, and more preferably $C_2$ to $C_4$ saturated or unsaturated alkylene, or combinations thereof, and wherein each $R^4$ independently represents H or a straight, or where possible branched or cyclic, $C_1$ to $C_6$ alkyl group, such as a $C_1$ to $C_4$ alkyl group, preferably H or a $C_1$ or $C_2$ alkyl group. It is preferable that the two $R^4$ groups are the same.

The alkylene group is as defined above. In particular, where the alkylene group contains 1 to 10 carbon atoms, it is to be understood that it includes each member of the range, i.e. the alkylene group can be a $C_1$, $C_2$, $C_3$, $C_4$, $C_5$, $C_6$, $C_7$, $C_8$, $C_9$ and/or $C_{10}$ alkylene. The alkyl group is as defined above.

In a particular feature, the alkylene group present in the aliphatic dicarboxylic acid or a mono- or diester derivative thereof is unbranched.

Aliphatic dicarboxylic acids or mono- or diester derivatives thereof that are of particular interest are adipic acid (hexanedioic acid), adipic acid monomethyl ester, adipic acid dimethyl ester, adipic acid monoethyl ester, adipic acid diethyl ester, succinic acid (butanedioic acid), succinic acid monomethyl ester, succinic acid dimethyl ester, succinic acid monoethyl ester, succinic acid diethyl ester, or combinations thereof, with adipic acid diethyl ester being particularly preferred. Copolymers formed from adipic acid or a mono- or diester derivative thereof may exhibit properties that are similar to PBAT, as discussed above.

All combinations of 2,4-pyridinedicarboxylic acid and/or 2,5-pyridinedicarboxylic acid or a mono- or diester of 2,4-pyridinedicarboxylic acid and/or 2,5-pyridinedicarboxylic acid, the diol, and, when present, the aliphatic dicarboxylic acid or a mono- or diester derivative thereof, are contemplated in the present invention.

The skilled person would understand that additional monomers may be incorporated into the copolymers of the invention produced by the process of the third aspect of the invention. Therefore, the process of the third aspect of the invention may also be for the formation of a copolymer comprising the polymerisation product of components (a), (b) and optionally (c) and, in addition, a heteroaromatic diacid (or a mono- or diester derivative thereof), aromatic diacid (or a mono- or diester derivative thereof), heteroaromatic diol and/or aromatic diol. Particular heteroaromatic and aromatic diacids that would be suitable for incorporation in the copolymers include terephthalic acid and 2,5-furandicarboxylic acid (or mono- or diester derivatives thereof).

Terephthalic acid

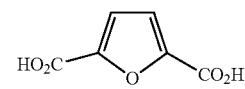
2,5-Furandicarboxylic acid

In a particular feature, the process is for the formation of a copolymer comprising the polymerisation product of
(a) 2,4-pyridinedicarboxylic acid (2,4-PDCA), 2,4-PDCA-2-methyl ester, 2,4-PDCA-4-methyl ester, 2,4-PDCA dimethyl ester, 2,4-PDCA-2-ethyl ester, 2,4-PDCA-4-ethyl ester, 2,4-PDCA diethyl ester, 2,5-pyridinedicarboxylic acid (2,5-PDCA), 2,5-PDCA-2-methyl ester, 2,5-PDCA-5-methyl ester, 2,5-PDCA dimethyl ester, 2,5-PDCA-2-ethyl ester, 2,5-PDCA-5-ethyl ester, 2,5-PDCA diethyl ester or a combination thereof;
(b) 1,2-ethanediol, 1,4-butanediol, or a combination thereof; and,
(c) adipic acid, adipic acid monomethyl ester, adipic acid dimethyl ester, adipic acid monoethyl ester, adipic acid diethyl ester, succinic acid, succinic acid monomethyl ester, succinic acid dimethyl ester, succinic acid monoethyl ester, succinic acid diethyl ester or a combination thereof
wherein the 2,4-pyridinedicarboxylic acid and/or 2,5-pyridinedicarboxylic acid is obtained by a process as defined in the first aspect of the invention, and/or the mono- or diester of 2,4-pyridinedicarboxylic acid and/or 2,5-pyridinedicarboxylic acid is obtained by a process as defined in the second aspect of the invention.

In another feature, the process is for the formation of a copolymer comprising the polymerisation product of
(a) 2,4-pyridinedicarboxylic acid (2,4-PDCA), 2,4-PDCA-2-methyl ester, 2,4-PDCA-4-methyl ester, 2,4-PDCA dimethyl ester, 2,4-PDCA-2-ethyl ester, 2,4-PDCA-4-ethyl ester, 2,4-PDCA diethyl ester, 2,5-pyridinedicarboxylic acid (2,5-PDCA), 2,5-PDCA-2-methyl ester, 2,5-PDCA-5-methyl ester, 2,5-PDCA dimethyl ester, 2,5-PDCA-2-ethyl ester, 2,5-PDCA-5-ethyl ester, 2,5-PDCA diethyl ester or a combination thereof; and
(b) 1,2-ethanediol, 1,4-butanediol, or a combination thereof
wherein the 2,4-pyridinedicarboxylic acid and/or 2,5-pyridinedicarboxylic acid is obtained by a process as defined in the first aspect of the invention, and/or the mono- or diester of 2,4-pyridinedicarboxylic acid and/or 2,5-pyridinedicarboxylic acid is obtained by a process as defined in the second aspect of the invention.

It may be advantageous to use diester derivatives of 2,4-pyridinedicarboxylic acid, 2,5-pyridinedicarboxylic acid and/or the aliphatic dicarboxylic acid to form the copolymers of the invention to avoid a possible interaction between the carboxylic acid groups of the monomers and the pyridine nitrogen of pyridinedicarboxylic acid. It may be particularly advantageous to use the same diester derivative of the 2,4-pyridinedicarboxylic acid and/or 2,5-pyridinedicarboxylic acid and the aliphatic dicarboxylic acid, i.e. 2,4-PDCA diethyl ester and/or 2,5-PDCA diethyl ester and adipic acid diethyl ester.

In a preferred feature of the third aspect of the invention, the process is for the formation of a copolymer comprising the copolyester of
(A) 2,4-pyridinedicarboxylic acid dimethyl ester or diethyl ester, or 2,5-pyridinedicarboxylic acid dimethyl ester or diethyl ester;
(B) 1,4-butanediol; and
(C) adipic acid dimethyl ester or diethyl ester
wherein the 2,4-pyridinedicarboxylic acid dimethyl ester or diethyl ester, or 2,5-pyridinedicarboxylic acid dimethyl ester or diethyl ester is obtained by a process as defined in the second aspect of the invention.

In an alternative preferred feature of the third aspect of the invention, the process is for the formation of a copolymer comprising the copolyester of
(A') 2,4-pyridinedicarboxylic acid dimethyl ester or diethyl ester, or 2,5-pyridinedicarboxylic acid dimethyl ester or diethyl ester; and
(B') 1,2-ethanediol
wherein the 2,4-pyridinedicarboxylic acid dimethyl ester or diethyl ester, or 2,5-pyridinedicarboxylic acid dimethyl ester or diethyl ester is obtained by a process as defined in the second aspect of the invention.

The copolymers may be prepared by reacting together at least one 2,4-pyridinedicarboxylic acid and/or 2,5-pyridinedicarboxylic acid or a mono- or diester of 2,4-pyridinedicarboxylic acid and/or 2,5-pyridinedicarboxylic acid with at least one diol and (when present) at least one aliphatic dicarboxylic acid or a mono- or diester derivative thereof simultaneously or concomitantly under standard conditions to form a copolymer. Such conditions include conditions suitable to perform, for instance, condensation reactions or transesterification reactions. The reaction type is of course dependent upon the terminal groups of the monomer starting materials. Preferably, the polymers are prepared by melt polymerisation or solvent-based condensation reactions.

A copolymer of the invention may be formed from about 1 to about 99 mol %, such as from about 10 to about 70 mol %, preferably from about 25 mol % to about 35 mol %, of 2,4-pyridinedicarboxylic acid and/or 2,5-pyridinedicarboxylic acid or a mono- or diester of 2,4-pyridinedicarboxylic acid and/or 2,5-pyridinedicarboxylic acid. A copolymer of the invention may be formed from about 1 to about 99 mol %, such as from about 20 to about 70 mol %, preferably from about 45 mol % to about 55 mol %, of diol. When present, a copolymer of the invention may be formed from about 1 to about 98 mol %, such as from about 10 to about 70 mol %, preferably from about 25 mol % to about 35 mol %, of aliphatic dicarboxylic acid a mono- or diester derivative thereof. The above mol % values are based upon the total amount of PDCA or mono- or diester derivative thereof, diol, and aliphatic dicarboxylic acid or mono- or diester derivative thereof. When the copolymer consists essentially of the pyridinedicarboxylic acid or mono- or diester of pyridinedicarboxylic acid, diol, and, when present, aliphatic dicarboxylic acids or mono- or diester derivatives thereof, it will be understood that the amount of diol will be about 50 mol % and the combined amount of the pyridinedicarboxylic acid or mono- or diester of pyridinedicarboxylic acid and aliphatic dicarboxylic acids or mono- or diester derivatives thereof will also be about 50 mol %.

As used herein the term "about" applies to all values, numeric or otherwise, whether or not explicitly indicated. Those values generally encompass or refer to a range of values that one skilled in the art would consider equivalent to the recited values (i.e. having the same function or result). Where the term "about" is used in relation to a numerical value, it can represent (in increasing order of preference) a 10%, 5%, 2% or 1% deviation from that value.

It will be understood by those skilled in the art that an excess of one of the monomers will typically result in polymer chains that terminate with that particular monomer.

It is understood that the ratios of monomers used in the process may reflect the ratios of monomers as present in a copolymer. This notwithstanding, it has been found to be advantageous to use an excess of at least one diol, in particular when a mono- or diester of 2,4-pyridinedicarboxylic acid and/or 2,5-pyridinedicarboxylic acid and/or a mono- or diester derivative of at least one aliphatic dicarboxylic acid is used. Without wishing to be bound by theory, this may advantageously help to ensure that the terminal groups of the copolymers comprise an alcohol. A suitable excess of at least one diol may be greater than about 5 mol %, such as greater than about 10 mol %, for instance greater than about 20 mol %, and preferably about 25 mol %, based upon the total amount of 2,4-pyridinedicarboxylic acid and/or 2,5-pyridinedicarboxylic acid or a mono- or diester of 2,4-pyridinedicarboxylic acid and/or 2,5-pyridinedicarboxylic acid and aliphatic dicarboxylic acid or mono- or diester derivative thereof in the reaction. Additional diol may be added during the process of the invention.

The process of the invention may be carried out in the presence of a catalyst. Typical catalysts useful in the second aspect of the invention may contain a metal, such as a transition metal, or an organometallic catalyst, and a Lewis acid, with aluminium, tin, antimony, titanium, and their alkoxides being particularly preferred. Titanium(IV) tert-butoxide and titanium(IV) isopropoxide are exemplary catalysts.

The process may be carried out in the presence of a suitable solvent, for example water or an organic solvent such as ethyl acetate, toluene, tetrahydrofuran, diethyl ether, dioxane, dimethylformamide, dimethylsulfoxide, an alcohol (such as methanol or ethanol), or mixtures thereof (including biphasic solvent systems, such as a mixture of water and an organic solvent). It is preferred that the process of the invention is carried out "neat", that is, no solvent is added to the reaction. The skilled person will understand that reacting together certain monomers (such as reacting together monomers comprising an ester group, i.e. an ethyl ester, with monomers comprising an alcohol group, in a transesterification reaction or condensation reaction) may form "solvent" (i.e. water or an alcohol, such as methanol or ethanol) as a result of the reaction. It is to be understood that the formation of a solvent during the reaction is not to be considered as solvent being added to the reaction. Such reactions are also considered to be carried out "neat". It may however be advantageous to use ethyl acetate as a solvent when 2,4-pyridinedicarboxylic acid, 2,5-pyridinedicarboxylic acid and/or an aliphatic dicarboxylic acid is used in the process.

The process may be performed at any suitable reaction temperature, for instance at room temperature or an elevated temperature. A preferred feature of the invention is that the reaction is carried out at one or more elevated temperatures. That is, the reaction is heated to a first reaction temperature at which the reaction remains for a first length of time. After this time, the reaction temperature is changed (i.e. raised or lowered) to a second reaction temperature at which the reaction remains for a second length of time. The process of changing the reaction temperature may be subsequently repeated. Suitable temperatures include temperatures from about 60° C. to about 250° C., such as from about 90° C. to about 220° C., i.e. from about 110° C. to about 180° C. Suitable times at which the reaction is held at a temperature are from about 1 hour to about 24 hours, such as from about 2 hours to about 19 hours, i.e. from about 3 hours or about 4 hours to about 17 hours.

The process of the invention may be performed at any suitable reaction pressure, for instance at atmospheric (or ambient) pressure or at an increased or reduced pressure. The terms "increased pressure" and "reduced pressure" are ones of the art and includes all pressure that are, respectively, above or below atmospheric (or ambient) pressure. In a preferred feature of the invention, the reaction pressure is changed (i.e. increased or decreased) during the process of the invention.

The change in reaction pressure may coincide with a change in the reaction temperature, as discussed above. Those skilled in the art will understand that a change in pressure and/or temperature does not take immediately effect within a reaction. Therefore, when the change in reaction pressure coincides with a change in the reaction temperature, the changes are made at about the same time or over the same or similar time period.

It is preferred that the reaction pressure is reduced over the course of the process of the invention. In particular, the process may be maintained at atmospheric pressure for a first time period, and then lowered to a reduced pressure for a second time period. The process of changing the reaction pressure may be subsequently repeated. Suitable reduced pressures include pressures from about 1 mbar to about 500 mbar such as from about 10 mbar to about 300 mbar i.e. from about 25 mbar to about 200 mbar.

In a particularly feature of the process of the invention, the process is performed at 110° C. for 4 hours at atmospheric pressure, then at 180° C. for 17 hours at 200 mbar, and then at 180° C. for 3 hours at 25 mbar.

The polymerisation reaction may be mixed, i.e. stirred, to ensure that a homogeneous reaction mixture is formed. Mixing the reaction may ensure, for instance, that a homogeneous, random polymer is formed. As is known, the formation of a polymer may result in an increase in the viscosity of a reaction mixture. Those skilled in the art will appreciate that a suitable mixing device should be employed.

A copolymer of the invention that is obtained by the process may be purified or separated from the reaction mixture by standard techniques, for instance by precipitation and filtration, evaporation, chromatography, and/or evaporation of solvents.

In general, the process of the third aspect of the invention may be operated as a batch process or operated as a continuous process or flow process, and may be conducted on any scale.

The processes disclosed herein may have the advantage that the copolymers of the invention, or precursors thereof, may be produced in a high yield, in a high purity, in less time, in a more convenient form (i.e. easier to handle), at a low cost, and from renewable sources. The processes may be considered "green" or "clean" and therefore have environmental benefits for both the processes and the copolymers of the invention.

In a fourth aspect of the invention there is provided a copolymer formed by a process as defined in the third aspect of the invention.

Such a copolymer is referred herein to as a copolymer of the invention.

The copolymer of the fourth aspect of the invention may be as illustrated in Formula I

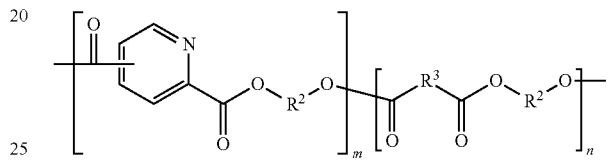

Formula I wherein $R^2$ and $R^3$ are as defined above, m is an integer greater than zero and n is an integer.

Particularly when carried out on an industrial scale, m may be from about 1 to about 400, such as from about 3 to about 350, for instance from about 5 to about 300, for example from about 7 to about 250, i.e. from about 10 to about 200.

As disclosed above, the aliphatic dicarboxylic acid or mono- or diester derivative thereof is optionally present in the copolymer. Thus, where the aliphatic dicarboxylic acid or mono- or diester derivative is not present, n is zero.

Where the aliphatic dicarboxylic acid or mono- or diester derivative is present, n is an integer greater than zero, i.e. one or more. Particularly when carried out on an industrial scale, n may be from about 1 to about 400, such as from about 3 to about 350, for instance from about 5 to about 300, for example from about 7 to about 250, i.e. from about 10 to about 200.

It is preferred that $R^2$ is a $C_2$ to $C_4$ alkylene, and $R^3$ is a $C_4$ to $C_6$ alkylene.

It will be apparent to those skilled in the art that the nomenclature used in, for instance, Formulae IA and IB does not denote the type of copolymer, i.e. a block copolymer, alternating copolymer, periodic copolymer, statistical copolymer or random copolymer. The copolymer of Formula I may be any copolymer type. However, it is preferred that it is a random copolymer.

The copolymer of the fourth aspect of the invention may also be as illustrated in Formula IA and/or Formula IB

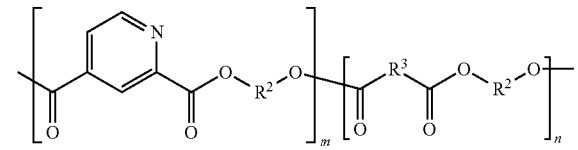

Formula IA

Formula IB

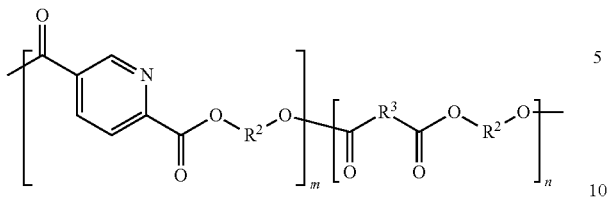

wherein R², R³, m and n are as defined above.

The copolymer of the fourth aspect of the invention may also be as illustrated in Formula II Formula II

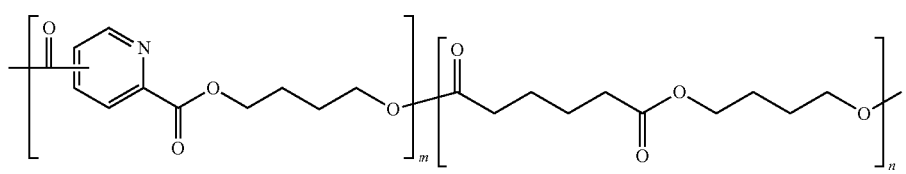

The copolymer of the fourth aspect of the invention may also be as illustrated in Formula IIA and/or Formula IIB Formula IIA Formula IIB wherein m and n are as defined above.

For the avoidance of any doubt, n may be zero in any of Formulae I to IIB. For example, when n is zero, Formula I, may be as illustrated in Formula IC Formula IC wherein m is as defined above including its preferred values.

Therefore, copolymer of the fourth aspect of the invention may also be as illustrated in Formula IIC and/or Formula IID Formula IIC

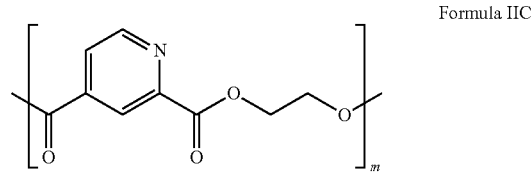

Formula IID wherein m is as defined above including its preferred values.

In a fifth aspect of the invention there is provided a copolymer comprising the copolyester of
(a) at least one pyridinedicarboxylic acid (PDCA) or a mono- or diester of pyridinedicarboxylic acid;
(b) at least one straight chain, alkylene diol; and
(c) at least one aliphatic dicarboxylic acid or a mono- or diester derivative thereof.

This copolymer is referred to herein as the copolymer of the invention.

The copolymer may comprise pyridinedicarboxylic acid (PDCA) or a mono- or diester of pyridinedicarboxylic acid selected from the group consisting of

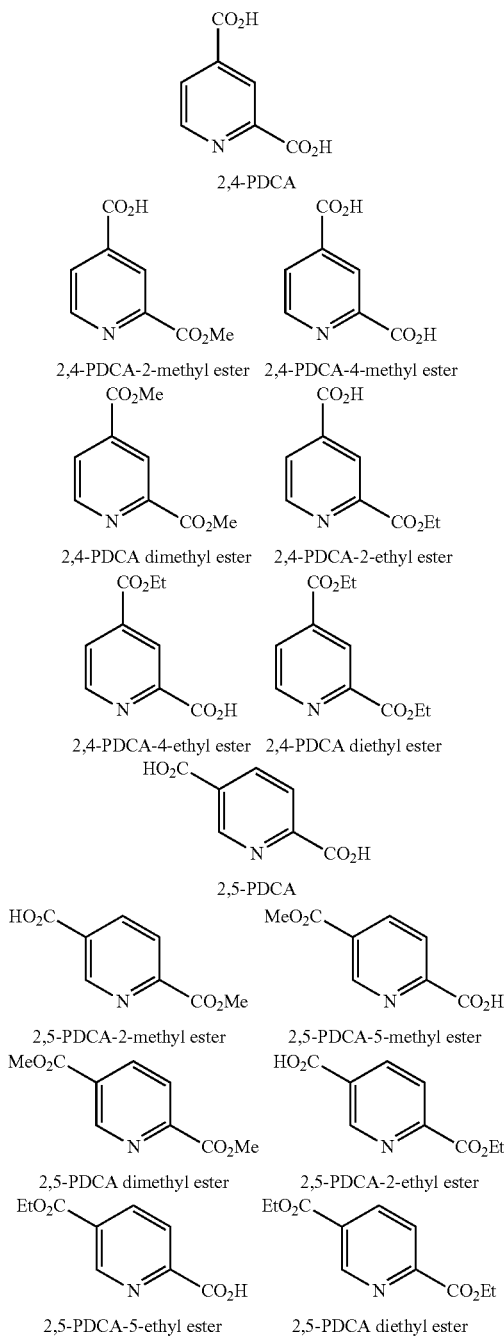

or a combination thereof.

The diol may be selected from the group consisting of 1,2-ethanediol, 1,4-butanediol, and a combination thereof.

The aliphatic dicarboxylic acid or a mono- or diester derivative thereof may be selected from the group consisting of adipic acid, adipic acid monomethyl ester, adipic acid dimethyl ester, adipic acid monoethyl ester, adipic acid diethyl ester, succinic acid, succinic acid monomethyl ester, succinic acid dimethyl ester, succinic acid monoethyl ester, succinic acid diethyl ester, and a combination thereof.

In a particular feature of the fifth aspect of the invention, the copolymer comprises the copolyester of
(A) 2,4-pyridinedicarboxylic acid dimethyl ester or diethyl ester, or 2,5-pyridinedicarboxylic acid dimethyl ester or diethyl ester;
(B) 1,4-butanediol; and
(C) adipic acid dimethyl ester or diethyl ester.

The copolymers may comprise the copolyester of components (a), (b) and (c) and, in addition, a heteroaromatic diacid (or a mono- or diester derivative thereof), aromatic diacid (or a mono- or diester derivative thereof), aromatic diol and/or aromatic diol.

There is also provided a process for the formation of a copolymer as defined in the fifth aspect of the invention, comprising reacting together components (a), (b) and (c).

The following apply equally to the third to fifth aspects of the invention. That is, the following features apply to both the copolymers formed by a process of the invention as defined in the third aspect of the invention, and the copolymers as defined in the fourth and fifth aspects of the invention.

A copolymer of the invention may have a molecular weight of from about 1,000 to about 100,000 gmol$^{-1}$, for example from about 2,000 to about 60,000 gmol$^{-1}$, such as from about 3,000 to about 50,000 gmol$^{-1}$, preferably from about 4,000 to about 30,000 gmol$^{-1}$, and most preferably from about 5,000 to about 20,000 gmol$^{-1}$. Such copolymers have particularly useful properties. The molecular weight of a copolymer of the invention was measured by Gel Permeation Chromatography (GPC) against a polystyrene standard as per Example 8.

A copolymer of the invention may have a first decomposition temperature within a range of from about 250° C. to about 350° C., and preferably from about 300° C. to about 340° C.

The copolymer may have a second decomposition temperature within a range of from about 350° C. to about 450° C., and preferably from about 360° C. to about 400° C. Without wishing to be bound by theory, the first decomposition temperature may relate to the decomposition of end-groups of the copolymers, whereas the second decomposition temperature may relate to the decomposition of the copolymer backbone. Simultaneous Thermal Analysis (STA) was used to determine the decomposition temperature of copolymer samples under an inert ($N_2$) atmosphere as defined in Example 7.

A copolymer of the invention may have a first glass transition temperature ($T_{g1}$) within a range of from about −50° C. to about 0° C., and preferably from about −40° C. to about −20° C. The copolymer may have a second glass transition temperature ($T_{g2}$) within a range of from about 20° C. to about 60° C., and preferably from about 30° C. to about 50° C.

A copolymer of the invention may have a melting point ($T_m$) within a range of from about 80° C. to about 150° C., and preferably from about 100° C. to about 140° C.

Differential Scanning Calorimetry (DSC) was used to determine the glass transition temperature (Tg) and the melting point ($T_m$) as defined in Example 7.

A copolymer of the invention may have a tensile strength in the range from about 1 MPa to about 50 MPa, such as from about 2 MPa to about 30 MPa, i.e. from about 3 MPa to about 15 MPa.

A copolymer of the invention may be stretched or elongated. The percentage elongation of the copolymer at its breaking point can range from about 1% to about 500%, such as from about 2% to about 300%, for example from about 3% to about 100% as based upon the original length of the copolymer.

A copolymer of the invention may have a Young's modulus in the range from about 10 MPa to about 500 MPa, such as from about 30 MPa to about 300 MPa, for example from about 50 MPa to about 150 MPa, i.e. from about 80 MPa to about 110 MPa.

Tensile strength, elongation and Young's modulus of the copolymers of the invention were measured as defined in Example 7.

Methods for testing the properties of copolymers, such as decomposition temperature, glass transition temperature, melting point, tensile strength etc. will be known to those skilled in the art.

A copolymer of the invention may be biodegradable and/or compostable. They may take less time to break down and be easier to recycle than current commercial polymers, such as PET and PBAT. Degradation may take place via a number of pathways including by hydrolysis and/or oxidation. Microorganisms, such as bacteria, yeasts, fungi, and also enzymatic processes also lead to biodegradation. For instance, enzymatic degradation of aliphatic polyesters including polyesters based upon succinic acid and aliphatic diols are known (see Tokiwa; Suzuki *Nature* 1977, 270, 76 to 78).

It has been found that pyridinedicarboxylic acids represent a viable aromatic alternative to the use of terephthalic acid in polymers, such as PET and PBAT. Thus, copolymers comprising pyridinedicarboxylic acids may be useful as replacements for PET or PBAT, and minimise the environmental and economic impact of current commercial polymers.

In a sixth aspect of the invention, there is provided a polymer blend comprising a copolymer of the invention. A polymer blend may be defined as a macroscopically homogeneous mixture of two or more different species of polymer. For instance, the polymer blends may be binary, ternary, quaternary or higher polymer blends.

The copolymers of the invention may be blended with, for instance, polylactic acid (PLA), starch, cellulose acetate, polyhydroxybutyrate (PHB), isotactic polypropylene (PP), poly(butylene succinate), poly-ε-caprolactone, poly(ethylene glycol), poly(ethylene oxide), and polymethyl methacrylate (PMMA). It is preferred that the copolymers of the invention are blended with PLA, starch and/or cellulose acetate.

A copolymer of the invention or polymer blends comprising the copolymer may take any physical form, for instance pellets, powders, sheets, fibres, or granules. It may be particularly advantageous for the copolymers or polymer blends to be pellets or granules to help processability or handling.

In a seventh aspect of the invention there is provided an article comprising a copolymer of the invention or a polymer blend as described above. The term "article" is synonymous with an item or product. Such articles include articles currently made from plastics and in particular those made using materials comprising or consisting of PET and PBAT.

All preferred features of the first to the seventh aspects of the invention relate to all other aspects of the invention mutatis mutandis.

Figure 1:
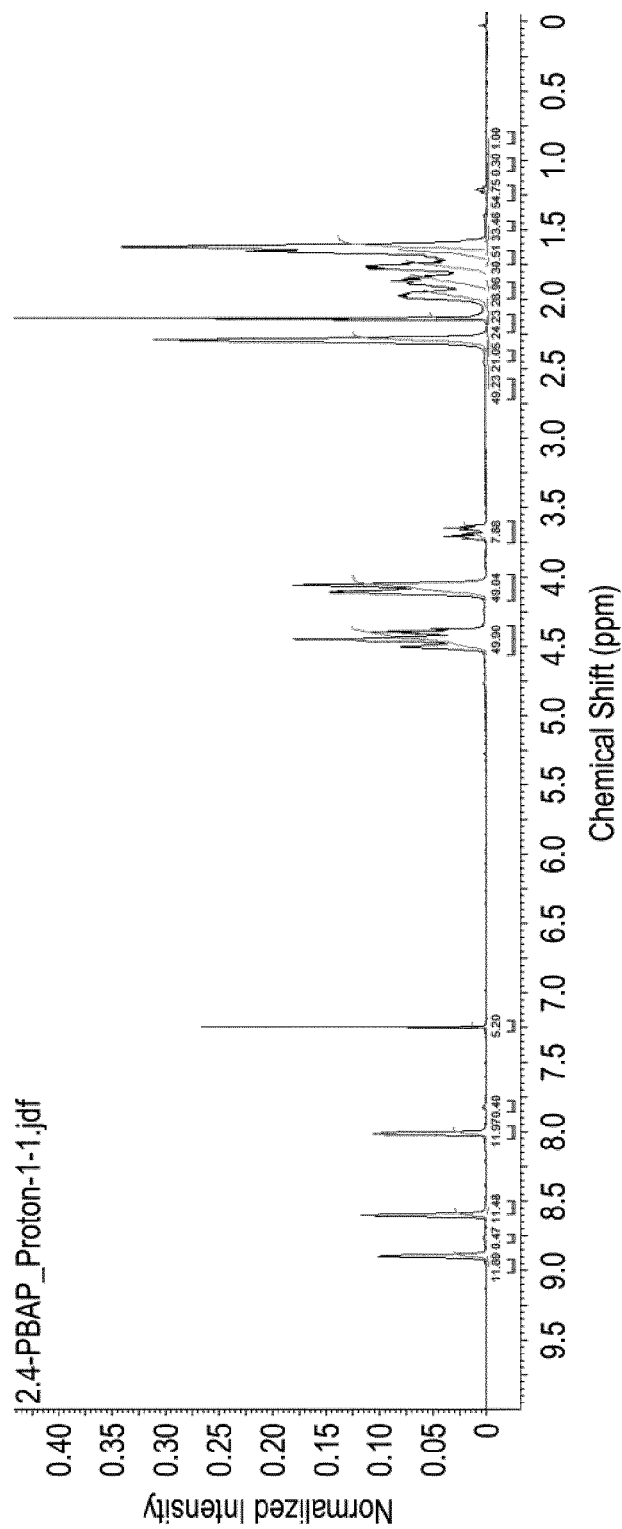
FIG. 1 shows the $^1$H NMR spectra for 2,4-polybutyrate adipate pyridinedicarboxylate (2,4-PBAP), i.e. a copolymer of the invention.

The following examples are merely illustrative examples of the invention described herein, and are not intended to be limiting upon the scope of the invention.

Any listing or discussion of an apparently prior-published document in this specification should not necessarily be taken as an acknowledgement that the document is part of the state of the art or common general knowledge. All references disclosed herein are to be considered to be incorporated herein by reference.

Example 1

Synthesis of 2,4-pyridinedicarboxylic acid (2,4-PDCA) and 2,5-pyridinedicarboxylic acid (2,5-PDCA)

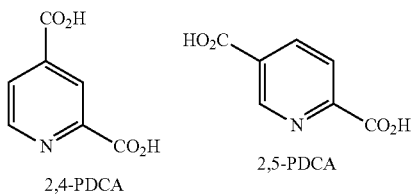 [SMILES: O=C(O)c1ccnc(C(=O)O)c1 ; O=C(O)c1ccc(C(=O)O)nc1]

2,4-PDCA      2,5-PDCA

Introduction of Recombinant Genes for 4,5-PCD, 2,3-PCD into R. jostii RHA1

The ligAB genes encoding *S. paucimobilis* protocatechuate 4,5-dioxygenase (Noda et al. *J. Bacteriol.* 1990, 172, 2704-2709) were cloned into a suitable expression vector used for inducible gene expression in *Rhodococcus*, using a thiostrepton inducer (Nakashima; Tamura *Appl. Environ. Microbiol.* 2004, 70, 5557-5568), generating a construct containing ligAB.

The praA gene encoding *Paenibacillus* sp. JJ-1b protocatechuate 2,3-dioxygenase (Kasai et al. *J. Bacteriol.* 2009, 191, 6758-6768) was cloned into an expression vector to give a construct containing praA.

The two constructs were each transformed into *Rhodococcus jostii* RHA1 via electroporation.

In order to verify expression of the recombinant genes, cell-free extract was obtained from cultures of *R. jostii* containing the ligAB gene and *R. jostii* containing the praA gene after induction with 1 μg/ml thiostrepton. Addition of the extract to solutions containing protocatechuic acid gave rise to a yellow colour in each case, corresponding to the meta-ring cleavage product, and absorbance changes of 0.2-0.45 absorbance units over 60 min at 410 nm and 350 nm for constructs containing ligAB and praA, respectively, corresponding to the literature values for the ring cleavage products for protocatechuate 4,5-dioxygenase (see Noda et al. above) and protocatechuate 2,3-dioxygenase (see Kasai et al. above), respectively.

Assay of Protocatechuate Ddioxygenase Activity

Cultures (5 mL) of *R. jostii* (ligAB) or *R. jostii* (praA) were grown for 24 hours at 30° C. in Luria-Bertani broth containing 50 μg/mL chloramphenicol, then induced with 1 μg/mL thiostrepton, and grown for a further 48 hours. Cell free-extract was prepared by centrifugation (microcentrifuge, 13,000 rpm, 5 min), then resuspension of the cell pellets in 75 μL of 20 mM Tris buffer pH 8.0, addition of lysozyme (5 μL or 5 mg/mL), incubation for 1 hour at 37° C., then sonication and centrifugation (microcentrifuge). Protocatechuic acid (2.5 mM, 800 μL) was added, and the solutions monitored at 350 nm for *R. jostii* (praA), giving absorbance changes of 0.29-0.42 after 60 min and a visible yellow colouration; and at 410 nm for *R. jostii* (ligAB), giving absorbance changes of 0.23-0.27 after 60 min and a slight yellow colouration.

Metabolite Production—General Methodology

Cultures (10 mL) of *R. jostii* (ligAB) or *R. jostii* (praA) were grown for 24 hours at 30° C. in M9 minimal media (6 g/L $Na_2HPO_4$, 3 g/L $KH_2PO_4$, 0.5 g/L NaCl, 1.0 g/L $NH_4Cl$, 2 mM $MgSO_4$, 0.5 mM $CaCl_2$) containing 50 μg/mL chloramphenicol and either 0.1% (w/v) vanillic acid or 1.0% (w/v) wheat straw lignocellulose, then induced with 1 μg/mL thiostrepton, and then grown for a further 7-11 days at 30° C., supplementing with 1 μg/mL thiostrepton at 48 hour intervals. Aliquots (1 mL) were removed, centrifuged (13,000 rpm, microcentrifuge, 5 min), and the supernatant extracted into ethyl acetate (1 mL). The ethyl acetate extract was injected onto a C18 Zorbax Eclipse plus (Agilent) reverse phase HPLC column on an Agilent 1200 Series system, and analysed by LC-MS using a Bruker HTC-Ultra ESI mass spectrometer. The HPLC solvents were water/ 0.1% trifluoroacetic acid (solvent A) and methanol/0.1% trifluoroacetic acid (solvent B). The applied gradient was 5% B for 5 min; 5-15% B over 10 min; 15-25% B for 8 min; and 25-100% B for 19 min, at a flow rate of 1.0 ml $min^{-1}$. 2,4-PDCA and 2,5-PDCA were detected by extracted ion analysis for fragment m/z 168.0, in positive ion mode, and were compared with authentic standards for 2,4-PDCA and 2,5-PDCA.

Production of 2,4-PDCA Using Vanillic Acid

Metabolite production was first tested on M9 minimal media containing 0.1% vanillic acid as carbon source and ammonium chloride as the nitrogen source. Extracts from *R. jostii* (ligAB) grown on M9 media containing 0.1% vanillic acid showed a new peak at retention time 9.8 min with m/z 167.7 ($MH^+$) and 189.7 ($MNa^+$) matching the retention time and mass spectrum of authentic 2,4-pyridinedicarboxylic acid. No metabolite production was observed using wild-type *R. jostii* RHA1 under the same conditions. Maximal 2,4-PDCA production was observed after 5 and 7 days fermentation. 2,4-PDCA production decreased after 10-12 days. The yield of 2,4-PDCA was determined by comparison with a standard curve of authentic material to be 112 mg per litre culture media.

Production of 2,5-PDCA Using Vanillic Acid

Extracts from *R. jostii* (praA) containing recombinant praA gene grown for 5 days on M9 media containing 0.1% vanillic acid also generated a new metabolite at retention time 10.0 min with m/z 167.7 ($MH^+$) and 189.7 ($MNa^+$) matching the retention time and mass spectrum of authentic 2,5-PDCA. Peak 2,5-PDCA production was observed after 5 days. The yield was determined to be 80 mg 2,5-PDCA per litre culture from LC-MS analysis.

Production of 2,4-PDCA and 2,5-PDCA Using Milled Wheat Straw Lignocellulose

The same constructs were then grown on M9 minimal media containing 1% milled wheat straw lignocellulose. Extracts from *R. jostii* (ligAB) gave the peak at 9.8 min corresponding to authentic 2,4-PDCA. Maximum production of 2,4-PDCA was observed at 5-7 days, and a yield of 90 mg/litre was determined by comparison with a standard curve for authentic 2,4-PDCA.

Extracts from *R. jostii* (praA) gave the peak at 10.0 min corresponding to authentic 2,5-PDCA. Maximum 2,5-PDCA production was observed at 5 days. A yield of 79 mg/L was determined by comparison with a standard curve for authentic 2,5-PDCA.

Bioreactor Fermentations—General Methodology

Cultures of *R. jostii* (ligAB) or *R. jostii* (praA) were grown at 30° C. in 2.5 L M9 minimal media (6 g/L $Na_2HPO_4$, 3 g/L $KH_2PO_4$, 0.5 g/L NaCl, 1.0 g/L $NH_4Cl$, 2 mM $MgSO_4$, 0.5 mM $CaCl_2$) containing 50 μg/mL chloramphenicol and either 0.1% (w/v) vanillic acid or 1.0% (w/v) wheat straw lignocellulose or 0.5% (w/v) Kraft lignin (from Billerud Korsnas Ltd, Sweden) in an Electrolab FerMac 3010 bioreactor. Fermentations were induced by addition of 1 μg/mL thiostrepton after 24 hours, and then grown for a further 3-8 days at 30° C., supplementing with 1 μg/mL thiostrepton at 48 hour intervals. After fermentation, cultures were harvested by centrifugation (6,000 g, 10 min), and the supernatant was applied to Amberlite™ IRA900 anion exchange column (100 mL volume), washed with water (200 mL), and then eluted with 0.5 M HCl (800 mL). 15×50 mL fractions were collected, and analysed by UV-vis spectroscopy for the presence of 2,4-PDCA ($\lambda_{max}$ 273 nm, $\varepsilon=3.1\times10^3$ $M^{-1}$ $cm^{-1}$) or 2,5-PDCA ($\lambda_{max}$ 271 nm, $\varepsilon=6.3\times10^3$ $M^{-1}$ $cm^{-1}$).

Bioreactor Fermentations—Production of 2,4-PDCA and 2,5-PDCA

The *R. jostii* (ligAB) construct was grown in a 2.5 L bioreactor in M9 minimal media containing 1% wheat straw lignocellulose for 9 days, reaching a maximum $OD_{600}=1.08$ after 5 days, and $OD_{600}=0.90$ after 9 days. After centrifugation of bacterial cells, the supernatant was applied to an Amberlite™ IRA900 anion exchange column (100 mL volume), washed with water, and then eluted with 0.5 M HCl. The eluted fractions showed absorbance maxima at 273 nm and 230 nm matching those of authentic 2,4-PDCA ($\varepsilon=3.1\times10^3$ $M^{-1}$ $cm^{-1}$), which was eluted in 15×50 mL fractions, with fractions 5 and 6 showing the greatest amount of product. The amount of 2,4-PDA present in the organic extracts after 9 days fermentation was 125 mg/L (estimated by LC-MS analysis). The yield of material after ion-exchange chromatography, based on UV-vis analysis, was 102 mg/L.

A fermentation of *R. jostii* (ligAB) in M9 minimal media containing 0.5% Kraft lignin over 4 days produced 2,4-PDCA (confirmed by HPLC analysis). Product isolation via Amberlite™ IRA900 anion exchange chromatography resulted in a yield of 53 mg/L 2,4-PDCA.

Growth of the *R. jostii* (praA) construct in the 2.5 L bioreactor in M9 minimal media containing 1% wheat straw lignocellulose over 9 days, followed by product isolation via Amberlite™ IRA900 anion exchange chromatography, yielded product fractions absorbing at 271 nm matching authentic 2,5-PDCA, with fractions 4 and 5 containing the most product. The amount of 2,5-PDCA present in organic extracts after fermentation for 9 days was 106 mg/L (estimated by LC-MS analysis). The yield of material after ion-exchange chromatography, based on UV-vis analysis, was 65 mg/L.

A summary of the yields of 2,4-PDCA and 2,5-PDCA is provided in Table 1.

TABLE 1

Yields of 2,4-PDCA and 2,5-PDCA

| Construct | Product | Scale | Carbon source for M9 minimal media | | |
|---|---|---|---|---|---|
| | | | 0.1% vanillic acid | 1% wheat straw | 0.5% Kraft lignin |
| *R. jostii* (ligAB) | 2,4-PDCA | 50 mL | 112 mg/L[a] (7 days) | 90 mg/L[a] (7 days) | — |
| | | 2.5 L bioreactor | — | 125 mg/L[a] (9 days) 102 mg/L[b] | 53 mg/L[b] (4 days) |
| *R. jostii* (praA) | 2,5-PDCA | 50 mL | 80 mg/L[a] (5 days) | 79 mg/L[a] (5 days) | — |
| | | 2.5 L bioreactor | — | 106 mg/L[a] (9 days) 65 mg/L[b] | — |

[a]yield estimated from LC-MS analysis of the fermentation broth as compared with authentic standard;
[b]yield of product after ion exchange chromatography, calculated using UV-vis absorption. Length of fermentation time indicated in brackets.

Example 2

Synthesis of 2,4-diethyl-2,4-pyridinedicarboxylate

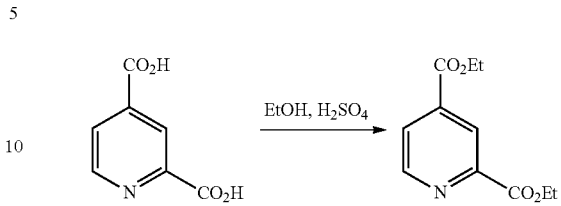

2,4-pyridinedicarboxylic acid (25.38 g; 150 mmol) was added to ethanol (1,300 mL). Aqueous sulfuric acid (2.54 g) was added. The mixture was heated at reflux (about 78° C.) for 15 hours, during which time water was removed from the reaction. The reaction progress was monitored using NMR spectroscopy. After the 2,4-diethyl-2,4-pyridinedicarboxylate had been formed in >97% purity by NMR, the reaction mixture was allowed to cool to ambient temperature and was extracted with 2-methyltetrahydrofuran. The combined organic layers were washed with a saturated aqueous brine solution and deionised water, and dried ($MgSO_4$). The organics were filtered and the volatiles were removed in vacuo to afford the title compound (24.49 g; 110 mmol; >99% conversion by GC).

Example 3

Synthesis of 2,5-diethyl-2,5-pyridinedicarboxylate

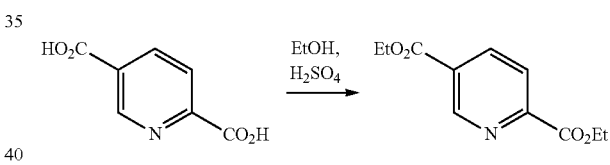

2,5-pyridinedicarboxylic acid (25.08 g; 150 mmol) was added to ethanol (1,800 mL). Aqueous sulfuric acid (1.32 g) was added. The mixture was heated at reflux (about 78° C.) for 58 hours, during which time water was removed from the reaction. The reaction progress was monitored using NMR spectroscopy. After the 2,5-diethyl-2,5-pyridinedicarboxylate had been formed in >97% purity by NMR, the reaction mixture was allowed to cool to ambient temperature and was extracted with 2-methyltetrahydrofuran. The combined organic layers were washed with a saturated aqueous brine solution and deionised water, and dried ($MgSO_4$). The organics were filtered and the volatiles were removed in vacuo to afford the title compound (26.61 g; 120 mmol; >99% conversion by GC).

General Methodology for the Formation of Copolymers

A 250 mL flange flask with 5 quick-fit ports was used. Stirring was achieved via a magnetic stirrer using a large precious metal stirrer bar. The rates of stirring were gradually decreased from the initial 400 rpm down to 200 rpm to avoid issues as a result of the increasing viscosity of the reaction mixture. All reagents were added to the reactor and warmed to 110 to 130° C. as described below to allow total melting and achieve miscibility. A flow of $N_2$ gas was applied for 20 minutes to purge the reagents and reactor of oxygen. The temperature was then increased to the desired point as stated below. After a further four hours of very low $N_2$ flow the gas line was removed, and a vacuum pump turned on, initially at a low vacuum (~200 mbar) but slowly increased as stated below.

Example 4

Synthesis of 2,4-polybutyrate adipate pyridinedicarboxylate (2,4-PBAP)

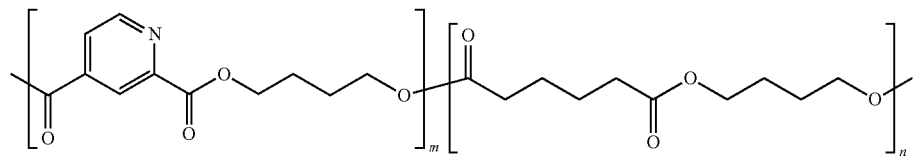

2,4-Diethyl-2,4-pyridinedicarboxylate (22.32 g; 100 mmol), diethyl adipate (20.23 g; 100 mmol), 1,4-butane diol (22.53, 250 mmol) and titanium(IV) tert-butoxide (0.77 mL; cat.) were combined. The reaction mixture was heated at 110° C. for 4 hours at atmospheric pressure with stirring at 400 rpm, 180° C. for 17 hours at 200 mbar and 350 rpm, and at 180° C. for 3 hours at 25 mbar and 250 rpm. The copolymer was formed (32.9 g). The $^1$H NMR spectra for 2,4-PBAP can be found at FIG. 1.

The ratio of 2,4-pyridinedicarboxylate:adipate was determined by $^1$H NMR to be 0.957:1. The molecular weight of the 2,4-PBAP was estimated using end-group analysis, wherein the ratio of end groups to those of the bulk polymer were calculated using $^1$H NMR to give the number of constitutional repeating units (CRU), which was estimated to be 9.60. One ideal CRU is 421.46 gmol$^{-1}$. Therefore, the molecular weight of the 2,4-PBAP was estimated to be 4,044.7 gmol$^{-1}$.

Example 5

Synthesis of 2,5-polybutyrate adipate pyridinedicarboxylate (2,5-PBAP)

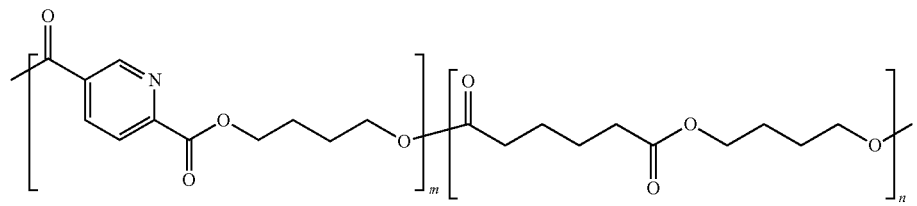

Figure 2:
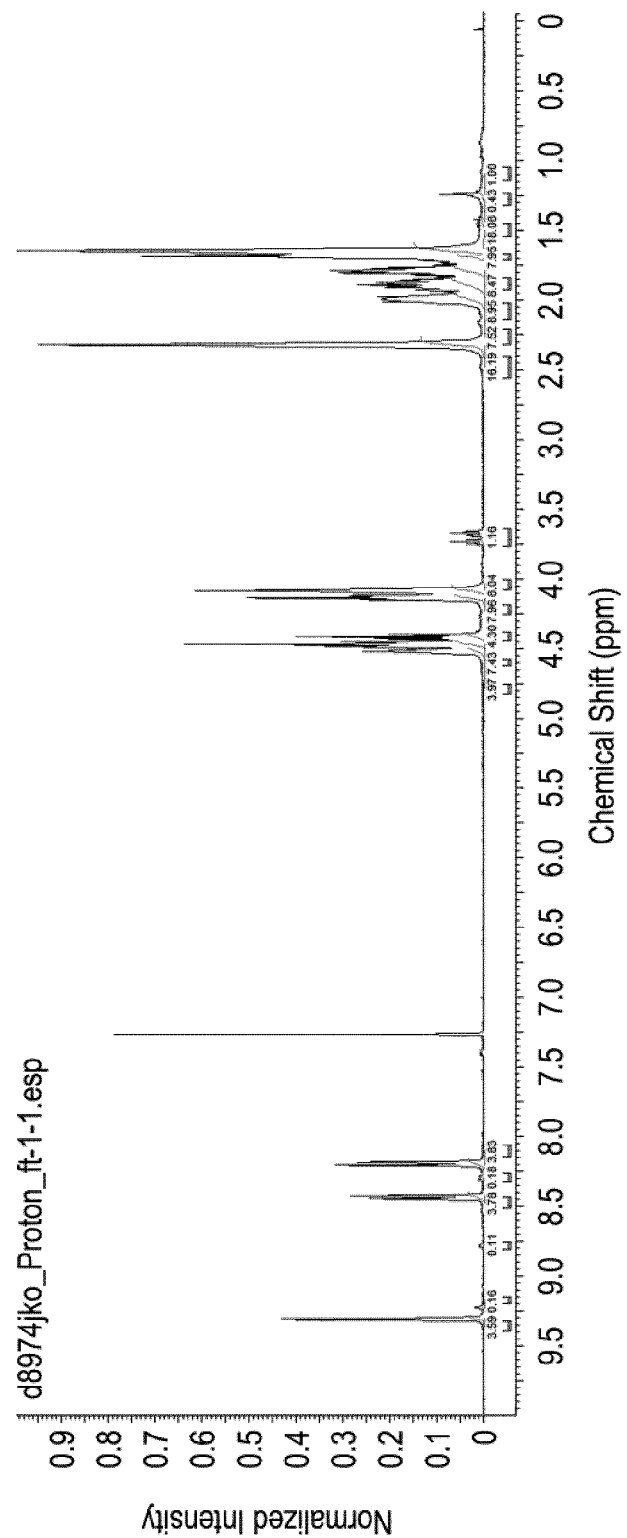
FIG. 2 shows the $^1$H NMR spectra for 2,5-polybutyrate adipate pyridinedicarboxylate (2,5-PBAP), i.e. a copolymer of the invention.

2,5-Diethyl-2,5-pyridinedicarboxylate (22.32 g; 100 mmol), diethyl adipate (20.23 g; 100 mmol), 1,4-butane diol (22.53, 250 mmol) and titanium(IV) tert-butoxide (0.77 mL; cat.) were combined. The reaction mixture was heated at 110° C. for 4 hours at atmospheric pressure with stirring at 400 rpm, 180° C. for 17 hours at 200 mbar and 350 rpm, and at 180° C. for 3 hours at 25 mbar and 250 rpm. The copolymer was formed (40.62 g). The $^1$H NMR spectra for 2,5-PBAP can be found at FIG. 2.

The molecular weight of the 2,5-PBAP was estimated by $^1$H NMR using end-group analysis as described for 2,4-PBAP. The ratio of 2,5-pyridinedicarboxylate:adipate was determined to be 0.92:1. The number of CRUs was estimated to be 10.15. One ideal CRU is 421.46 gmol$^{-1}$. Therefore, the molecular weight of the 2,5-PBAP was estimated to be 4,278.8 gmol$^{-1}$.

Comparative Example 6

Synthesis of Polybutyrate Adipate Terephthalate (PBAT)

Figure 3:
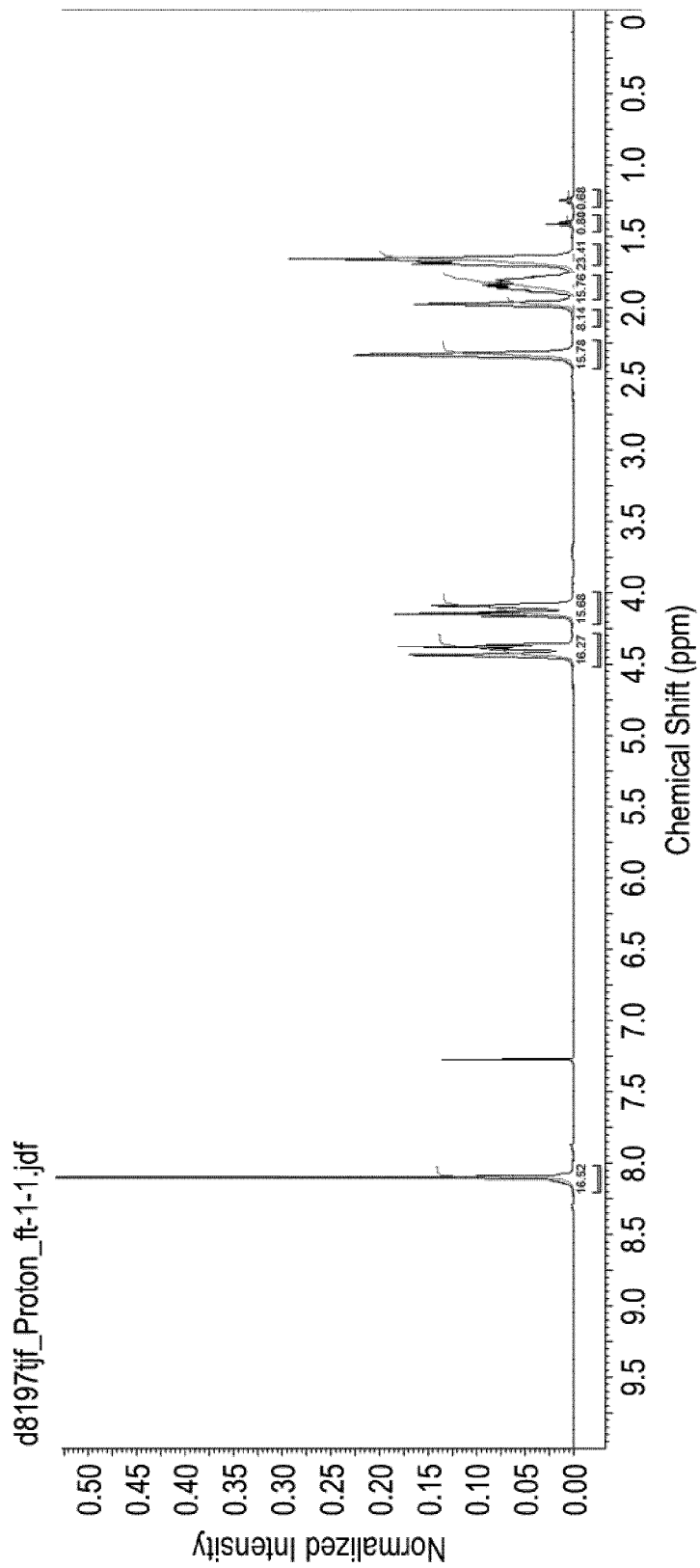
FIG. 3 shows the $^1$H NMR spectra for polybutyrate adipate terephthalate (PBAT) (Comparative Example 6).

Diethyl terephthalate (22.22 g; 100 mmol), diethyl adipate (20.23 g; 100 mmol), 1,4-butane diol (22.73, 230 mmol) and titanium(IV) tert-butoxide (0.77 mL; cat.) were combined. The reaction mixture was heated at 130° C. for 2 hours at atmospheric pressure with stirring at 400 rpm, 180° C. for 2 hours at atmospheric pressure and 400 rpm, 180° C. for 17 hours at 200 mbar and 350 rpm, and at 180° C. for 3 hours at 25 mbar and 250 rpm. The copolymer was formed (40.51 g). The $^1$H NMR spectra for PBAT can be found at FIG. 3.

The molecular weight of the PBAT was estimated by $^1$H NMR using end-group analysis as described for 2,4-PBAP. The ratio of terephthalate:adipate was determined to be 1.047:1.

The number of CRUs was estimated to be 16.4. One ideal CRU is 420.45 gmol$^{-1}$. Therefore, the molecular weight of the PBAT was estimated to be 6,893 gmol$^{-1}$.

Figure 4:
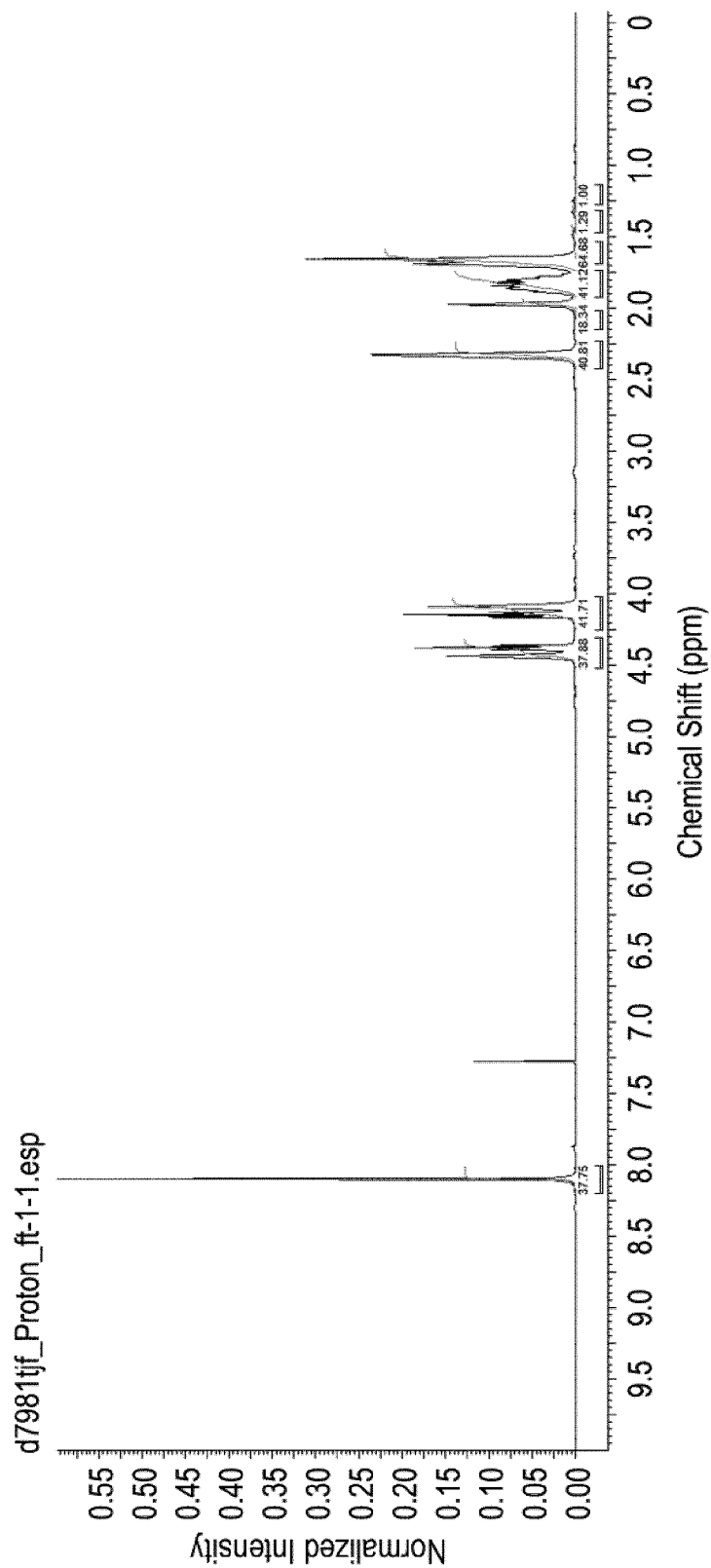
FIG. 4 shows the $^1$H NMR spectra for commercial PBAT.

PBAT is available commercially under a range of trade names. The molecular weight of one particular commercial PBAT was estimated by $^1$H NMR using end-group analysis as described for 2,4-PBAP. The ratio of terephthalate:adipate was determined to be 0.93:1. The number of CRUs was estimated to be 25.7. One ideal CRU is 420.45 gmol$^{-1}$. Therefore, the molecular weight of the commercial PBAT was estimated to be 10,809 gmol$^{-1}$. The $^1$H NMR spectra for commercial PBAT can be found at FIG. 4.

Example 7

Thermal Analysis of Polymers Using (STA and DSC)

The thermal stability of cured copolymer was analysed using Simultaneous Thermal Analysis (STA) using a Stanton Redcroft STA 625. Approximately 10-20 mg of copolymer was heated from ambient temperature to 625° C. at a heating rate of 10° C. min-1 under nitrogen. Typically, two distinct decompositions were observed; when present, the first may be the decomposition of end-groups and is thus often small, the second may be the major decomposition of the copolymer backbone. The results can be found in Table 2.

TABLE 2

STA analysis of polymers

Figure 5:
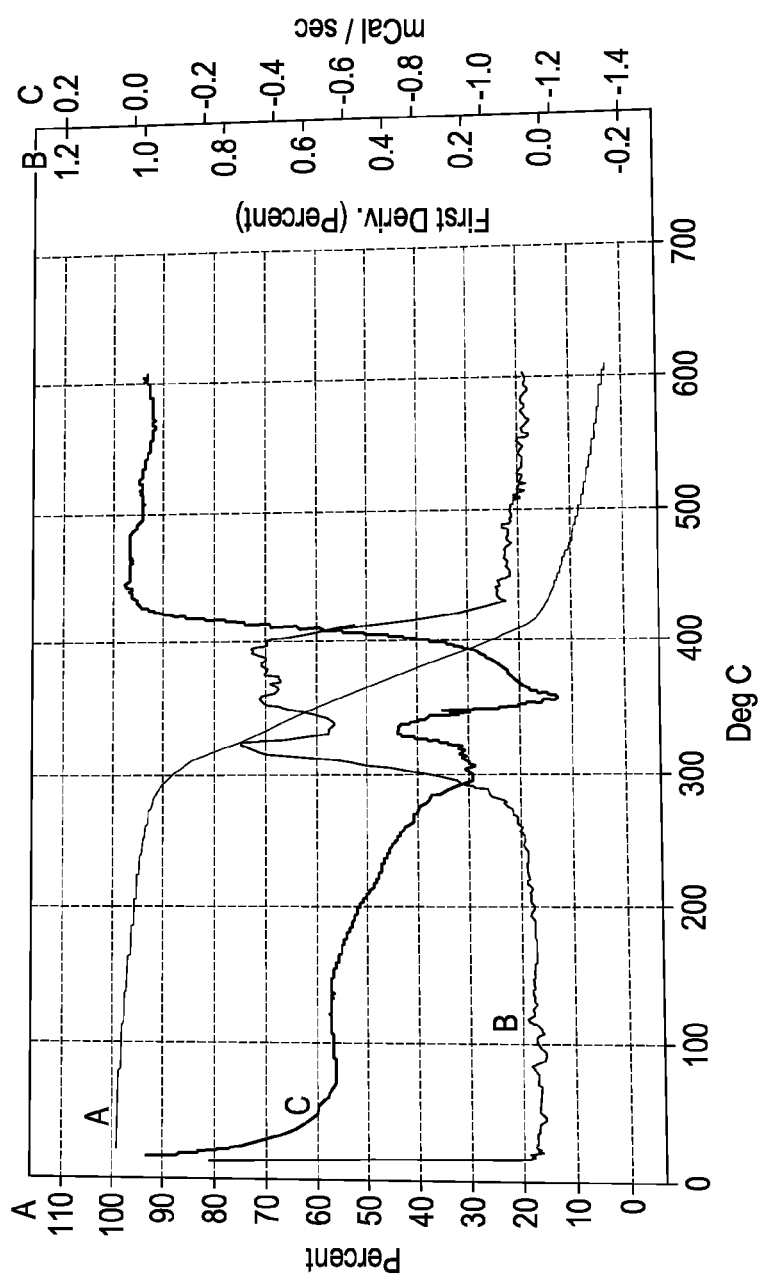
FIG. 5 shows the Simultaneous Thermal Analysis (STA) trace for 2,4-PBAP.
Figure 6:
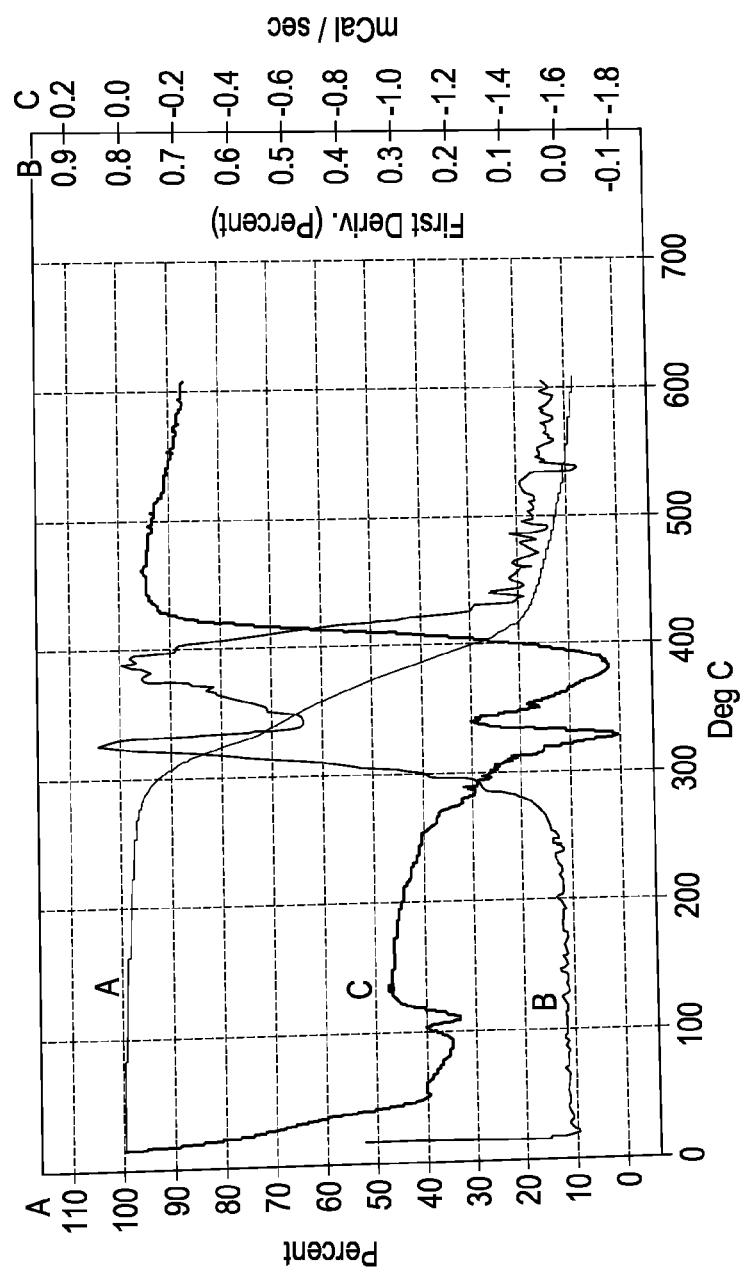
FIG. 6 shows the STA trace for 2,5-PBAP.
Figure 7:
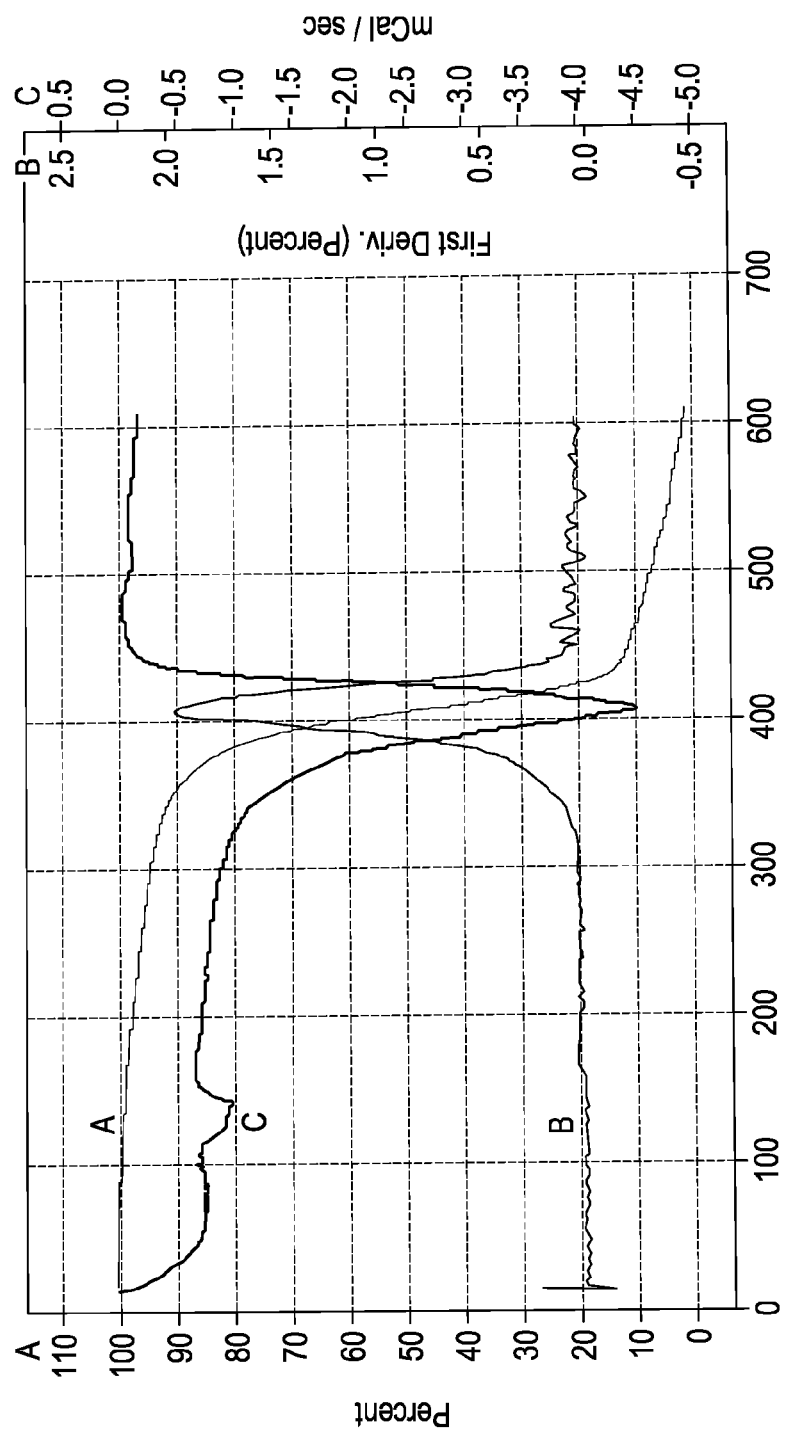
FIG. 7 shows the STA trace for PBAT (Comparative Example 6).
Figure 8:
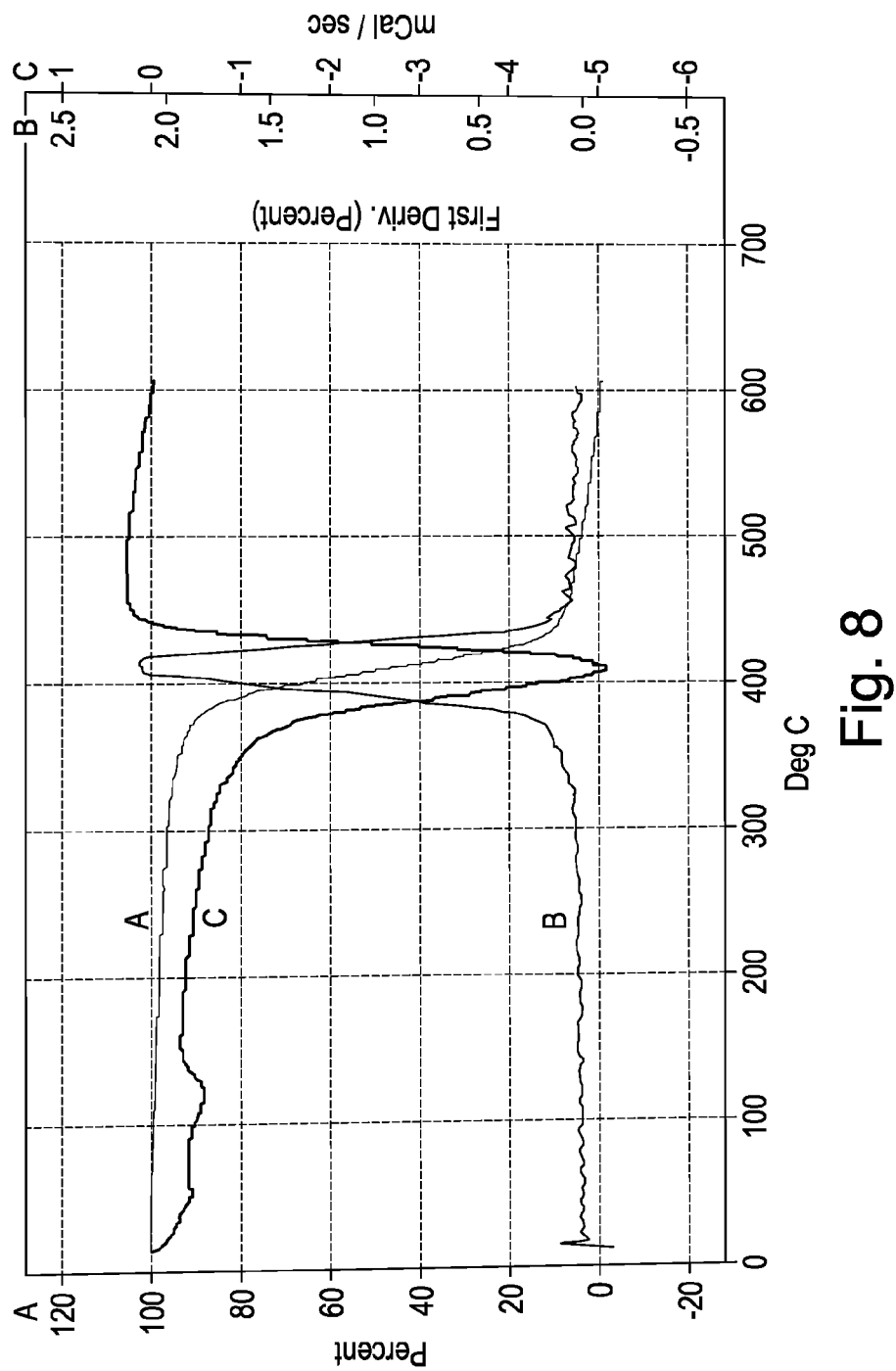
FIG. 8 shows the STA trace for commercial PBAT.

| Copolymer | Temperature of 5 wt % loss ° C. | Temperature of 1$^{st}$ decomp. ° C. | Temperature of 2$^{nd}$ decomp. ° C. | STA trace |
|---|---|---|---|---|
| 2,4-BPAP | 304.7 | — | 356.2 | FIG. 5 |
| 2,5-PBAP | 289.1 | 328 | 381.5 | FIG. 6 |
| Comparative Example 6 | 289.5 | — | 406.0 | FIG. 7 |
| Commercial PBAT | 341.5 | — | 409.5 | FIG. 8 |

The glass transition temperature ($T_g$) and melting point ($T_m$) of the copolymers were obtained by Differential Scanning Calorimetry (DSC) analysis using a TA Instruments Q2000 DSC. Indium was used as the standard to calibrate the temperature and heat capacity. Copolymer samples (7-10 mg) were sealed in T zero aluminum hermetic DSC pans. The method was carried out under a constant flow of dry nitrogen of 50 mL/min, at 10° C./min over a temperature range of −80° C. to 250° C. The results can be found in Table 3. The DSC traces can be found at FIG. 9.

TABLE 3

DSC analysis of copolymers

| Copolymer | $T_{g1}$ ° C. | $T_{g2}$ ° C. | $T_m$ ° C. |
|---|---|---|---|
| 2,4-BPAP | −31.7 | — | — |
| 2,5-PBAP | −35.3 | 41.9 | 105.9 |
| Comparative Example 6 | −39.5 | 42.4 | 134.6 |
| Commercial PBAT | −30.1 | 45.4 | 122.2 |

Example 8

Gel Permeation Chromatography (GPC)

The molecular weight ($M_n$ and $M_w$) and polydispersity ($Pd_i$) data as generated by GPC can be found in Table 4. GPC was conducted on an Agilent SECurity GPC System 1260 Infinity using THF as the solvent, a polystyrene standard, and a light scattering detector.

TABLE 4

GPC analysis of copolymers

Figure 9:
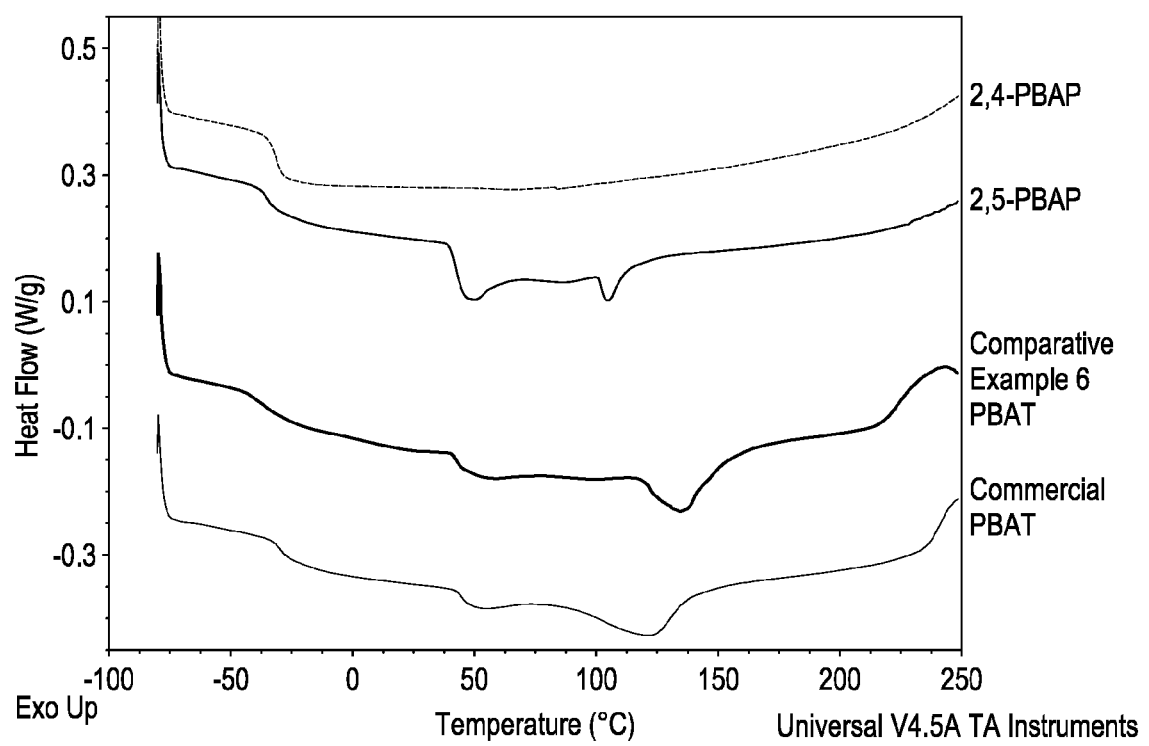
FIG. 9 shows Differential Scanning Calorimetry (DSC) traces for 2,4-PBAP, 2,5-PBAP, PBAT (Comparative Example 6) and commercial PBAT.
Figure 10:
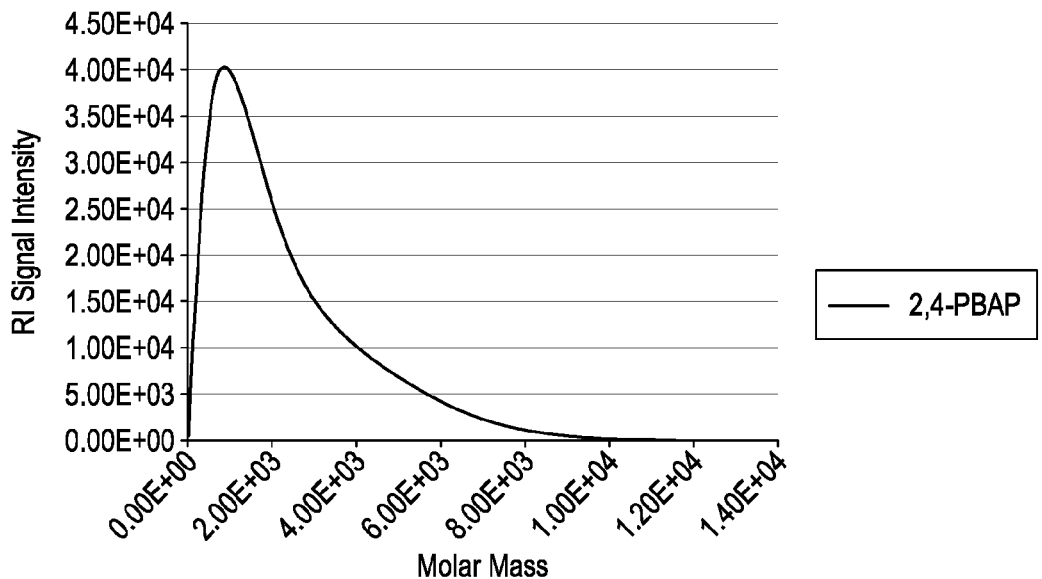
FIG. 10 shows the Gel Permeation Chromatography (GPC) spectra for 2,4-PBAP.
Figure 11:
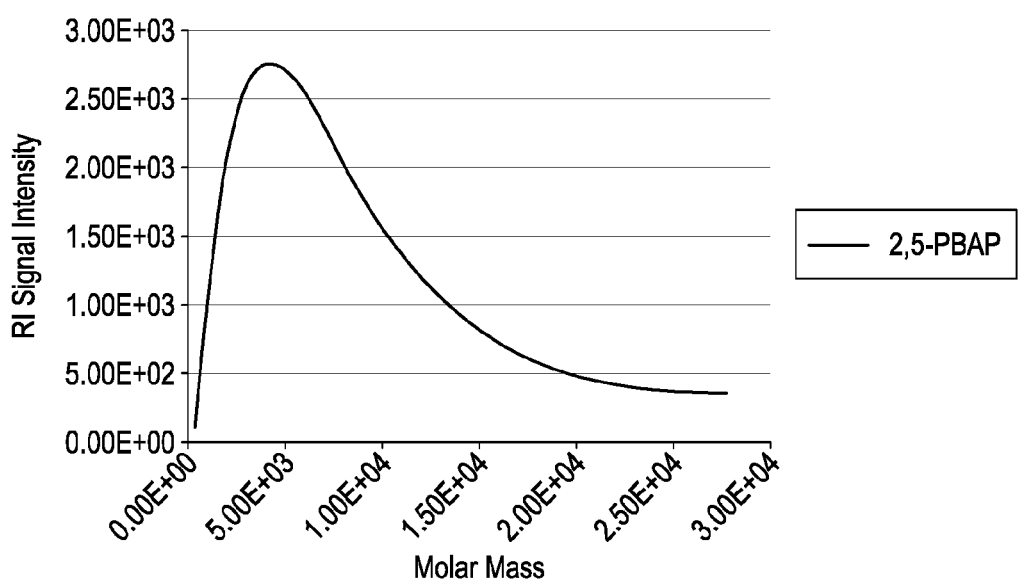
FIG. 11 shows the GPC spectra for 2,5-PBAP.
Figure 12:
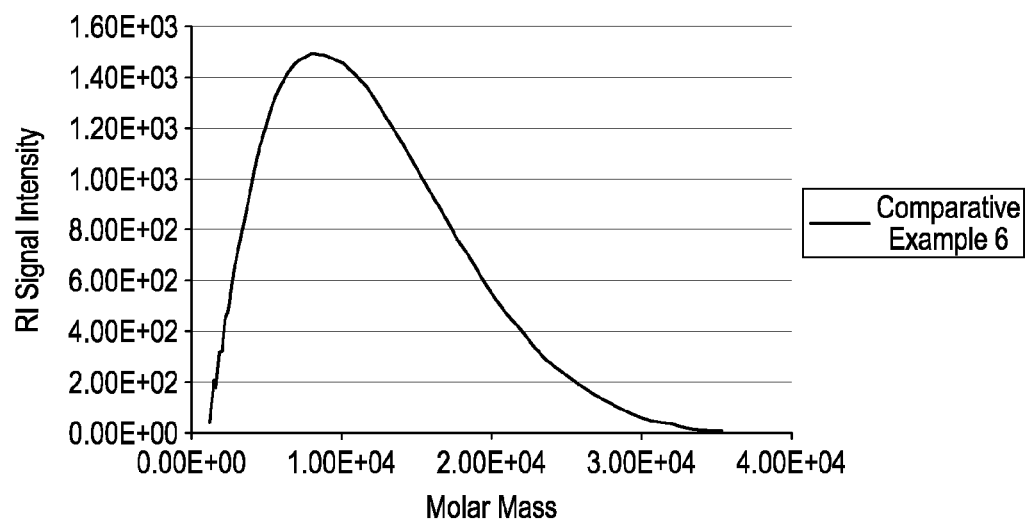
FIG. 12 shows the GPC spectra for PBAT (Comparative Example 6).
Figure 13:
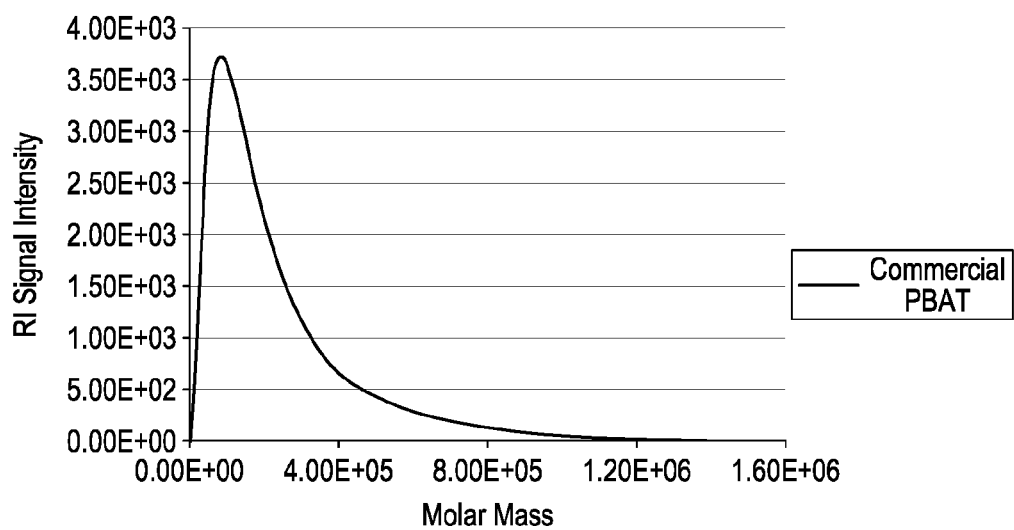
FIG. 13 shows the GPC spectra for commercial PBAT.
Figure 14:
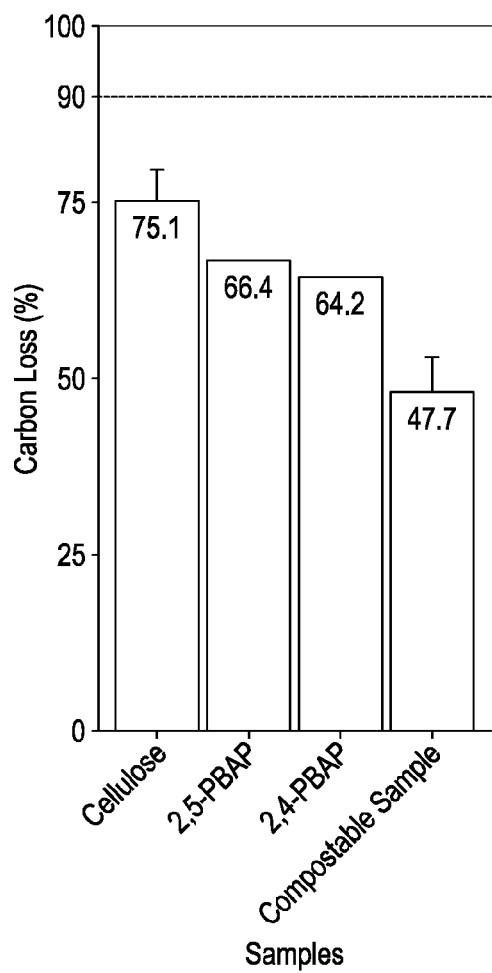
FIG. 14 shows that under the biodegradation test conditions outlined in Example 10. 2,4-PBAP and 2,5-PBAP result in greater percentage carbon loss (66.4% and 64.2%, respectively) than a compostable sample (47.7%), after 40 days. The 90% level set for biodegradation in the test accounts for a +1-10% statistical variability of the experimental measurement, which one would expect virtually complete biodegradation in the composting environment of the test.
Figure 15:
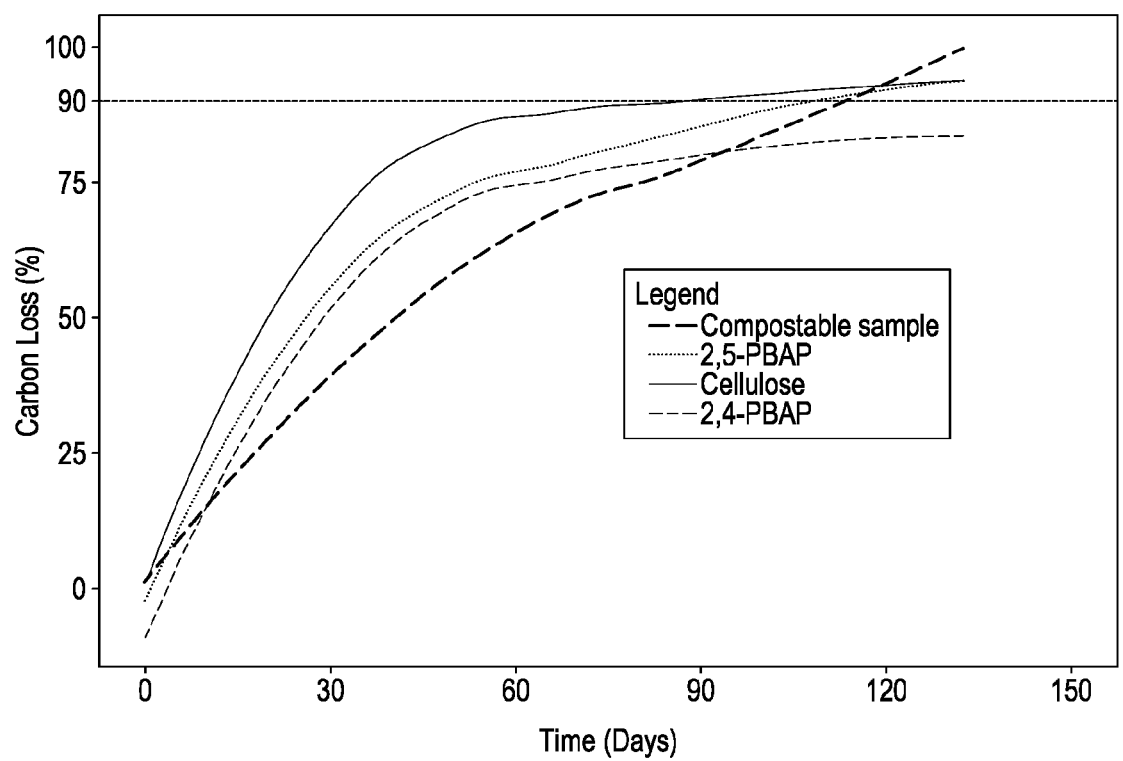
FIG. 15 shows that under the biodegradation test conditions outlined in Example 10, 2,4-PBAP and 2,5-PBAP rapidly lose carbon at a rate faster than that of a compostable sample. 2,5-PBAP reaches 90% carbon loss after about 105 days, which is fast than that of a compostable sample. The 90% level is as defined for FIG. 14 above.
Figure 16:
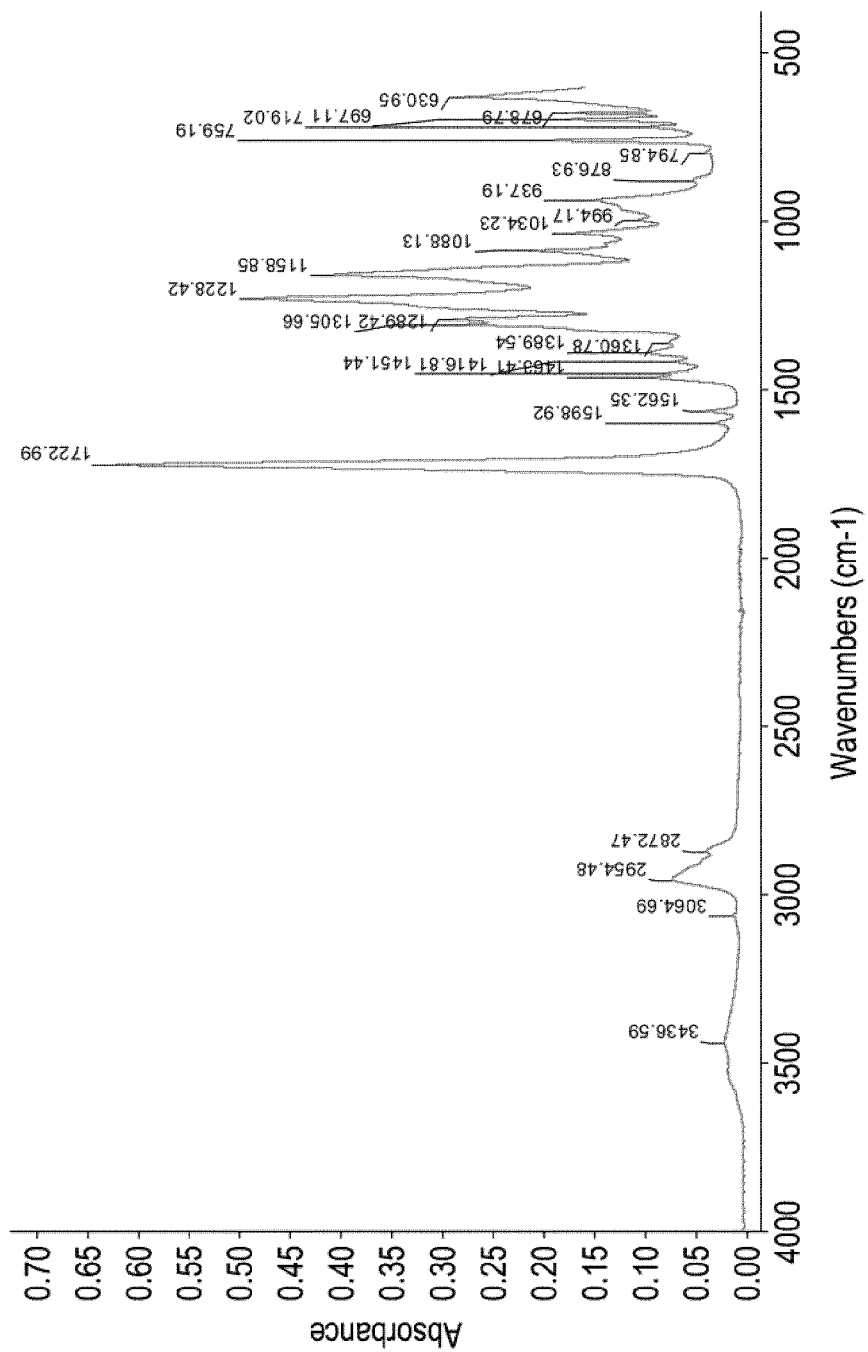
FIG. 16 shows the attenuated total reflectance Fourier transform infrared spectra (ATR-FTIR) of 2,4-PBAP using a Thermo Nicolet Nexus FT-IR spectrometer coupled with a Continuum IR microscope.
Figure 17:
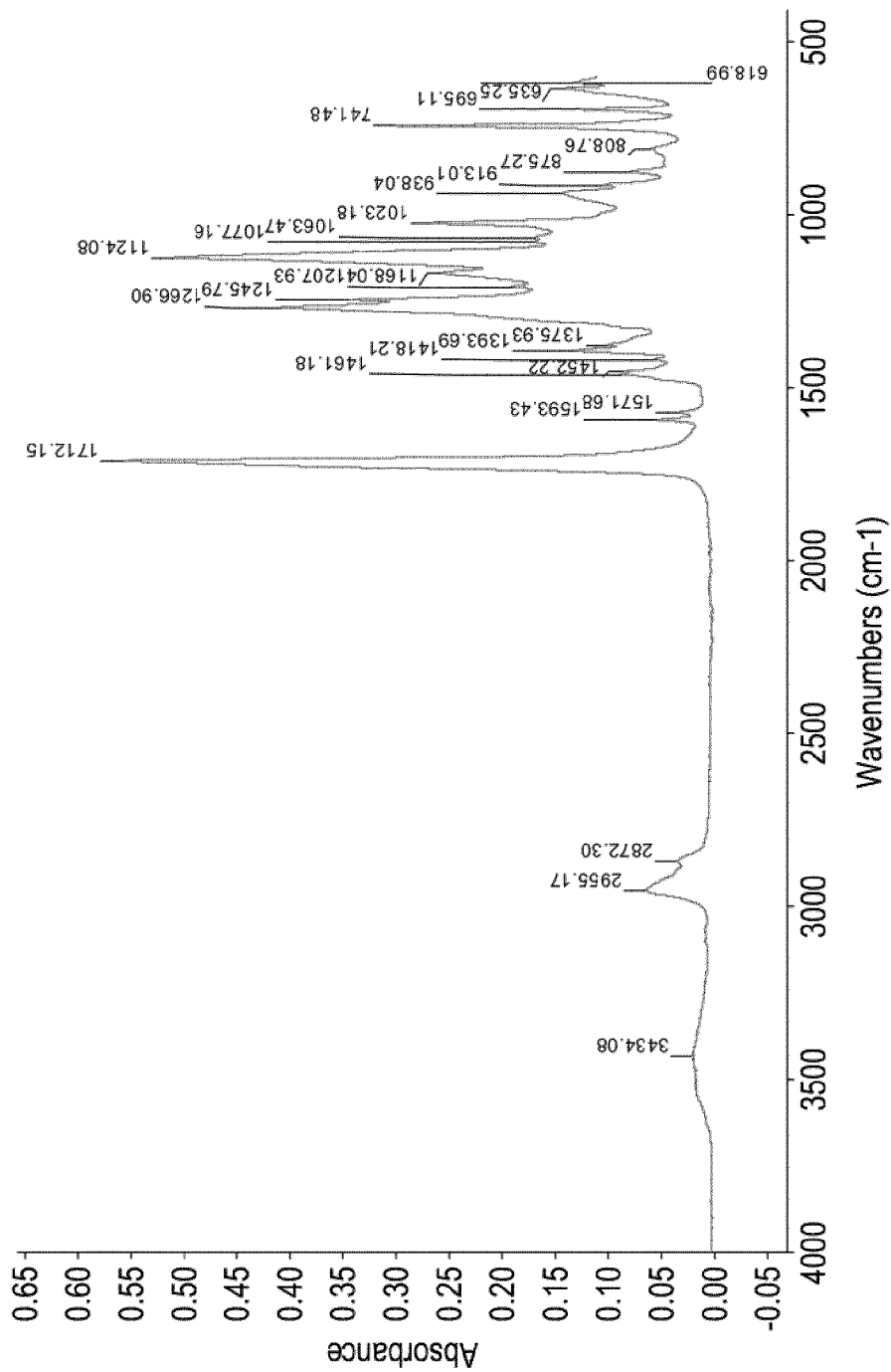
FIG. 17 shows the attenuated total reflectance Fourier transform infrared spectra (ATR-FTIR) of 2,5-PBAP using a Thermo Nicolet Nexus FT-IR spectrometer coupled with a Continuum IR microscope.
Figure 18:
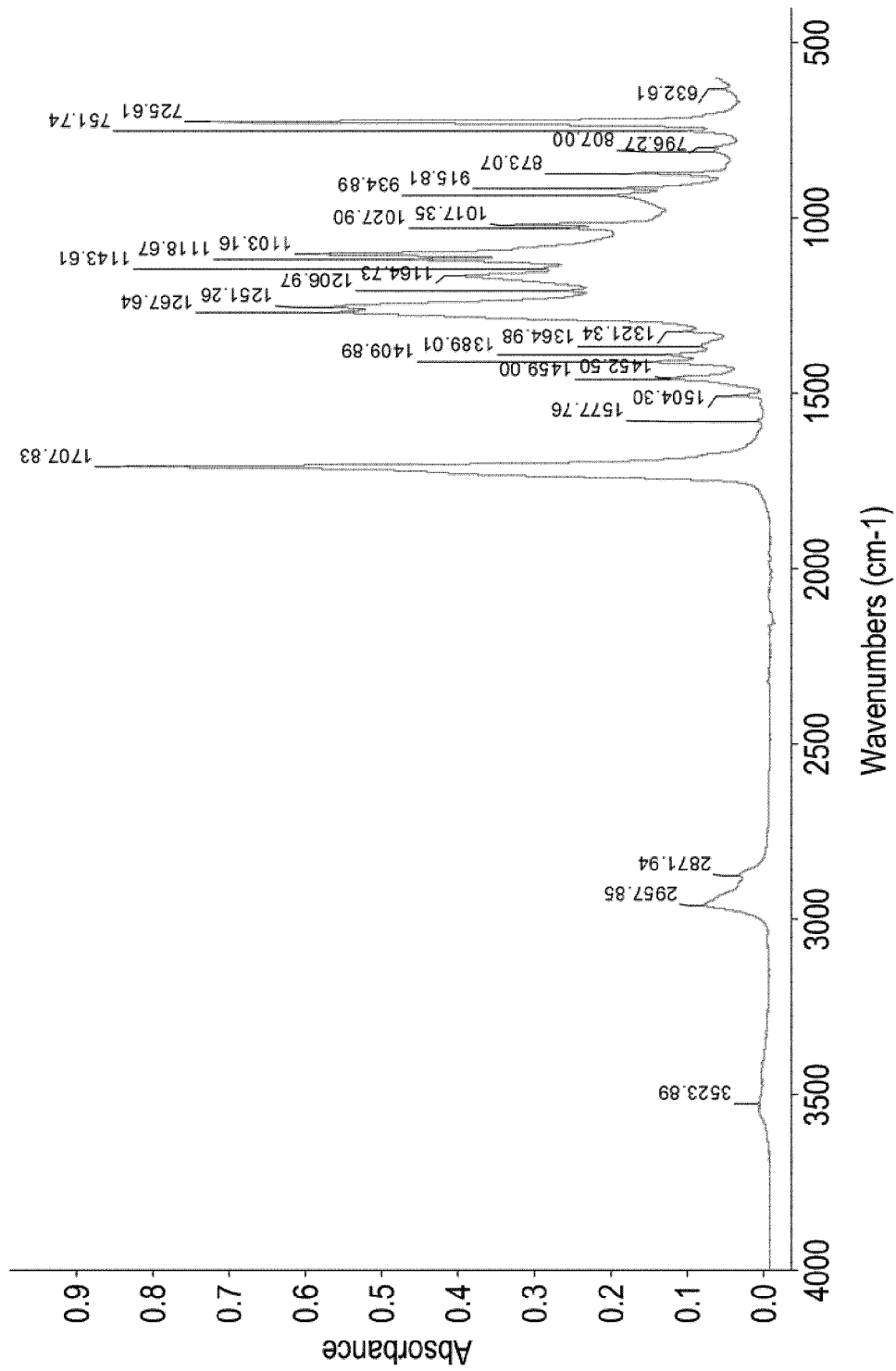
FIG. 18 shows the attenuated total reflectance Fourier transform infrared spectra (ATR-FTIR) of commercial PBAT using a Thermo Nicolet Nexus FT-IR spectrometer coupled with a Continuum IR microscope.

| Copolymer | $M_n$ | $M_w$ | $Pd_i$ | GPC chromatogram |
|---|---|---|---|---|
| 2,4-PBAP | 323.3 | 1,109 | 3.4 | FIG. 9 |
| 2,5-PBAP | 2,448 | 5,186 | 2.11 | FIG. 10 |
| Comparative Example 6 | 5,582 | 8,615 | 1.544 | FIG. 11 |
| Commercial PBAT | 42,190 | 113,100 | 2.680 | FIG. 12 |

Example 9

Tensile Strength Measurement

Mechanical properties including tensile strength, elongation at break and Young's modulus of samples are summarised in Table 5. Film samples were prepared by heating about 8 g of copolymer in a fan-assisted oven at 160° C. for 15 min (180° C. for PBAT). The resulting films were cut into standard dumb-bell shapes (60 mm×10 mm). Film thickness was in the region of 1.5-2.0 mm. Tensile studies were conducted in triplicate using an Instron 3367 universal testing machine fitted with 1000 N capacity load cell. The initial grip separation was set at 35 mm and the crosshead speed was 20 mm/min. The results reported were the average of the three measurements (the elongation at break was obtained automatically from the software). Commercial PBAT is a typical elastomer with elongation over 293%. It has the highest tensile strength over 19.5 MPa and good Young's modulus of 100.8 MPa.

TABLE 5

Tensile strength measurement of copolymers

| Copolymer | Tensile strength MPa | Elongation at break % | Young's Modulus MPa |
|---|---|---|---|
| 2,4-PBAP | — | — | — |
| 2,5-PBAP | 2.8 ± 0.4 | 5.2 ± 0.3 | 90.6 ± 14.0 |
| Comparative Example 6 | 4.8 ± 0.5 | 2.3 ± 0.2 | 269.8 ± 0.2 |
| Commercial PBAT | >19.5 | >293.1 | 100.8 |

The 2,4-PBAP and 2,5-PBAP copolymers produced are soft like that of the commercial PBAT. The expected ratio of PDCA to adipate of about 1:1 has been incorporated into the copolymer. The observed molecular weight of 2,4-PBAP, 2,5-PBAP and comparative example 6 (PBAT) are significantly lower than that of commercial PBAT. This is expected given the relatively small scale on which the copolymerisations were conducted and will be higher in a full scale production process. The NMR data provides an indication of the relative number of constitutional repeating units (CRU) and hence an indication of molecule weight, though the GPC provides more accurate values.

The differences in the data obtained for the copolymers of the invention and the commercial BPAT may be partly attributed to a lack of branching in 2,4-PBAP and 2,5-PBAP.

Those skilled in the art will recognise or be able to ascertain using no more than routine experimentation many equivalents to the specific embodiments described herein. The scope of the present embodiments described herein is not intended to be limited to the above description, but rather is as set forth in the appended claims. Those of ordinary skill in the art will appreciate that various changes and modifications to this description may be made without departing from the spirit or scope of the present invention, as defined in the following claims.

Example 10

Stabilised green waste compost is matured in a composting bin under controlled aeration conditions. Before use, the mature compost is sieved on a screen of 5 mm. The fine fraction forms the inoculum with a total solids content of approximately 50-55% and the volatile content of the total solids is more than 30%.

The standard and control materials are mixed with the inoculum in a ratio of approximately 1 to 1.5 parts of total solids to 6 parts of total solids and introduced into a reactor. These reactors are closed and put into an incubator. The temperature of the reactors is maintained at 58° C. +/−2° C. Pressurised air is pumped through a gas flow controller and blown into the composting vessel at the bottom through a porous plate. During biodegradation, solid carbon of the test sample is converted into $CO_2$.

The gas leaving each individual reactor is analysed at regular intervals for $CO_2$ and $O_2$ concentrations. As the flow rate is continually measured, the cumulative $CO_2$ production can be determined. The percentage of biodegradation is determined as the percentage of solid carbon of the test compound that is converted into $CO_2$.

The invention claimed is:

1. A method comprising combining:
   (a) at least one pyridinedicarboxylic acid (PDCA) or a mono- or diester of pyridinedicarboxylic acid;
   (b) at least one diol; and
   (c) optionally, at least one aliphatic dicarboxylic acid or a mono- or diester derivative thereof,
   under conditions suitable for condensation, transesterification or polymerization to produce a copolymer comprising residues of (a), (b) and optionally (c), wherein:
   the method is catalyzed by an organic acid, an inorganic acid or a metal;
   the method comprises holding (a), (b) and optionally (c) at a temperature of about 60° C. to about 250° C.; and
   the method comprises holding (a), (b) and optionally (c) at a pressure of about 1 mbar to about 500 mbar.

2. The method as claimed in claim 1, wherein the copolymer comprises the copolyester of
   (a) at least one pyridinedicarboxylic acid or a mono- or diester of pyridinedicarboxylic acid;
   (b) at least one diol; and
   (c) at least one aliphatic dicarboxylic acid or a mono- or diester derivative thereof.

3. The method as claimed in claim 1, wherein the pyridinedicarboxylic acid or a mono- or diester of pyridinedicarboxylic acid is

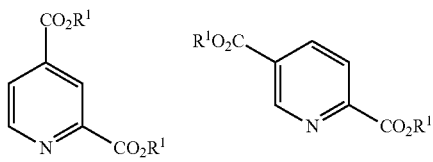

wherein each $R^1$ independently represents H or a straight, branched or cyclic, $C_1$ to $C_6$ alkyl group.

4. The method as claimed in claim 1, wherein the pyridinedicarboxylic acid or a mono- or diester of pyridinedicarboxylic acid is selected from the group consisting of

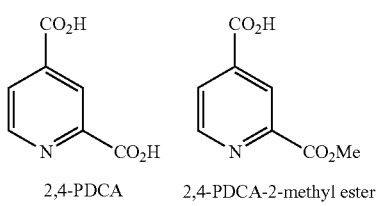

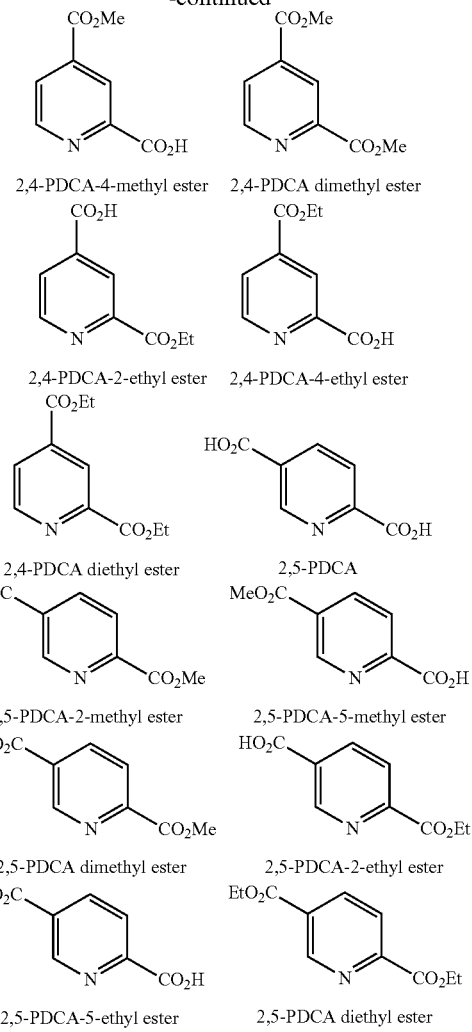

or a combination thereof.

5. The method as claimed in claim 1, wherein the diol is

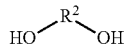

wherein $R^2$ is a straight, branched or cyclic $C_2$ to $C_{10}$ alkylene.

6. The method as claimed in claim 1, wherein the diol is selected from the group consisting of 1,2-ethanediol, 1,4-butanediol, and a combination thereof.

7. The method as claimed in claim 1, wherein the aliphatic dicarboxylic acid or a mono- or diester derivative thereof is

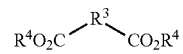

wherein $R^3$ is a straight, branched or cyclic, $C_1$ saturated or $C_2$ to $C_{10}$ saturated or unsaturated alkylene, and wherein each $R^4$ independently represents H or a straight, branched or cyclic, $C_1$ to $C_6$ alkyl group.

8. The method as claimed in claim 1, wherein the aliphatic dicarboxylic acid or a mono- or diester derivative thereof is selected from the group consisting of adipic acid, adipic acid monomethyl ester, adipic acid dimethyl ester, adipic acid monoethyl ester, adipic acid diethyl ester, succinic acid, succinic acid monomethyl ester, succinic acid dimethyl ester, succinic acid monoethyl ester, succinic acid diethyl ester, and a combination thereof.

9. The method as claimed in claim 1, wherein the copolymer comprises the copolyester of
  (A) pyridinedicarboxylic acid dimethyl ester or diethyl ester;
  (B) 1,4-butanediol; and
  (C) adipic acid dimethyl ester or diethyl ester.

10. The method as claimed in claim 1, wherein the copolymer comprises the copolyester of
  (A') pyridinedicarboxylic acid dimethyl ester or diethyl ester; and
  (B') 1,4-butanediol or 1,2-ethanediol.

11. The method as claimed in claim 1, wherein the copolymer comprises the copolyester of
  (a) from 1 to 99 mol % of at least one pyridinedicarboxylic acid or a mono- or diester of pyridinedicarboxylic acid;
  (b) from 1 to 99 mol % of at least one diol; and
  (c) when present, from 1 to 98 mol % of at least one aliphatic dicarboxylic acid or a mono- or diester derivative thereof.

12. The method as claimed in claim 1, wherein the pyridinedicarboxylic acid is obtained by a process comprising the steps of
  (i) contacting a protocatechuate dioxygenase produced by *Rhodococcus jostii* with 3,4-dihydroxybenzoic acid to form a ring-opened product of 3,4-dihydroxybenzoic acid; and
  (ii) cyclising the ring-opened product of step (i) with a nitrogen source to form the pyridinedicarboxylic acid.

13. The method as claimed in claim 12, wherein
  (a) the pyridinedicarboxylic acid is 2,4-pyridinedicarboxylic acid, and wherein the ring-opened product is 4-carboxy-2-hydroxymuconate-6-semialdehyde (CHMS)

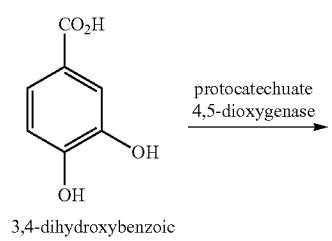

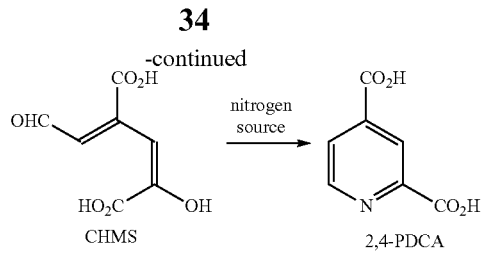

or
  (b) the pyridinedicarboxylic acid is 2,5-pyridinedicarboxylic acid, and wherein the protocatechuate dioxygenase is protocatechuate 2,3-dioxygenase, and the ring-opened product is 5-carboxy-2-hydroxymuconate-6-semialdehyde (5-CHMS)

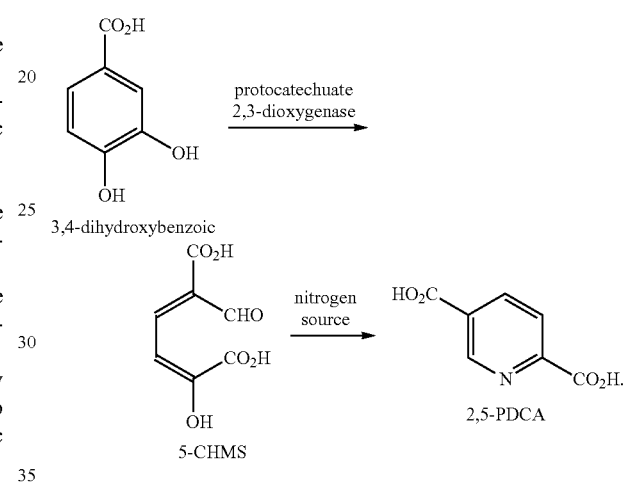

14. The method as claimed in claim 1, wherein the mono- or diester of pyridinedicarboxylic acid is obtained by a process comprising the step of
  (i) providing pyridinedicarboxylic acid; and
  (ii) adding an alcohol and a catalyst to the pyridinedicarboxylic acid provided in step (i),
  wherein the pyridinedicarboxylic acid is obtained by
  (iii) contacting a protocatechuate dioxygenase produced by *Rhodococcus jostii* with 3,4-dihydroxybenzoic acid to form a ring-opened product of 3,4-dihydroxybenzoic acid; and
  (iv) cyclising the ring-opened product of step (i) with a nitrogen source to form the pyridinedicarboxylic acid.

15. The method as claimed in claim 1, wherein the method comprises holding (a), (b) and optionally (c) at about 60° C. to about 250° C. for a time period from about 1 hour to about 24 hours.

* * * * *